US012716900B2

(12) United States Patent
Snyder et al.

(10) Patent No.: US 12,716,900 B2
(45) Date of Patent: Aug. 25, 2026

(54) SYSTEM FOR DETERMINING AN UNDERLYING CAUSE OF ANEMIA

(71) Applicant: Quest Diagnostics Investments LLC, Secaucus, NJ (US)

(72) Inventors: Louis Michael Snyder, Framingham, MA (US); Jeffrey Samuel Dlott, Reston, VA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 936 days.

(21) Appl. No.: 17/798,823

(22) PCT Filed: Feb. 10, 2021

(86) PCT No.: PCT/US2021/017481

§ 371 (c)(1),
(2) Date: Aug. 10, 2022

(87) PCT Pub. No.: WO2021/163209

PCT Pub. Date: Aug. 19, 2021

(65) Prior Publication Data

US 2023/0083600 A1 Mar. 16, 2023

Related U.S. Application Data

(60) Provisional application No. 62/972,835, filed on Feb. 11, 2020.

(51) Int. Cl.
*G01N 33/68* (2006.01)
*G01N 33/80* (2006.01)
*G01N 15/01* (2024.01)

(52) U.S. Cl.
CPC ......... *G01N 33/6893* (2013.01); *G01N 33/80* (2013.01); *G01N 2015/014* (2024.01); *G01N 2800/22* (2013.01); *G01N 2800/60* (2013.01)

(58) Field of Classification Search
CPC .... G01N 33/6893; G01N 33/80; G01N 33/84; G01N 33/82; G01N 2015/014; G01N 2800/22; G01N 2800/60; A61P 7/06; C07K 14/805
USPC .................................. 436/63, 66, 81, 86, 10
See application file for complete search history.

(56) References Cited

U.S. PATENT DOCUMENTS 6,524,858 B1 * 2/2003 Zelmanovic ........... G01N 15/14 436/166
7,209,835 B1 * 4/2007 Pearlman ............... G16H 10/40 706/54
2003/0073635 A1 4/2003 Roddiger et al.
2007/0172956 A1 * 7/2007 Magari ................ G01N 33/721 436/66
2008/0213277 A1 9/2008 Sasu et al.
2010/0076787 A1 3/2010 Naylor et al.
2010/0266591 A1 10/2010 Bugelski et al.
2013/0236566 A1 * 9/2013 Higgins ............. G01N 33/6893 424/646
2018/0280432 A1 10/2018 Gupta
2019/0091218 A1 3/2019 May

FOREIGN PATENT DOCUMENTS

WO 2011/057744 * 5/2011
WO WO-2011/057744 A1 5/2011

OTHER PUBLICATIONS

Anonymous, “Anemia Diagnostic Cascading Reflex (test code 37931),” Quest Diagnostics Incorporated, Feb. 1, 2022, retrieved from https://testdirectory.questdiagnostics.com/test/test-algorithm-detail/TS_Anemia_Cascading_Reflex_Fig/anemia-diagnostic-cascading-reflex-test-code-37931?p=td on Feb. 19, 2024, 3 pgs.
Anonymous, “Blood Disorders Day Anemia,” Jan. 1, 2016, retrieved from https://blooddisordersday.com/wp-content/uploads/2023/01/Blood-Day-ANEMIA-Pathway.pdf on Feb. 21, 2024, 1 pg.
Cascio et al., “Anemia Evaluation and Diagnostic Tests,” Medical Clinics of North America, vol. 101, No. 2, Mar. 1, 2017, pp. 263-284.
Jansen, “Diagnosis of anemia—A synoptic overview and practical approach,” Transfusion and Apheresis Science, Elsevier Science, London, GB, vol. 58, No. 4, Jul. 5, 2019, pp. 375-385.
Kaufman et al., “Revised prevalence estimate of possible Hereditary Xerocytosis as derived from a large U.S. Laboratory database,” American Journal of Hematology, New York, NY, US, vol. 93, No. 1, Nov. 23, 2017, pp. E9-E12.
Lanier et al., “Anemia in Older Adults,” American Family Physician, Oct. 1, 2018, pp. 437-442.
Partial European Search Report dated Mar. 4, 2024, in EP 21753290.2.
Yenilmez et al., “Laboratory Approach to Anemia,” in “Current Topics in Anemia,” Feb. 7, 2018, InTech, pp. 235-253.
International Search Report and Written Opinion dated Apr. 27, 2021, in PCT/US2021/017481.

* cited by examiner

*Primary Examiner* — Maureen Wallenhorst
(74) *Attorney, Agent, or Firm* — DUANE MORRIS LLP

(57) ABSTRACT

Disclosed herein are automated processes and systems for determining an underlying cause of anemia. Also disclosed herein are processes and systems for determining an underlying cause of microcytic anemia, normocytic anemia, and macrocytic anemia. Additionally disclosed herein are methods of treating the underlying cause of anemia in an individual in need thereof.

23 Claims, 5 Drawing Sheets

FIG. 1A

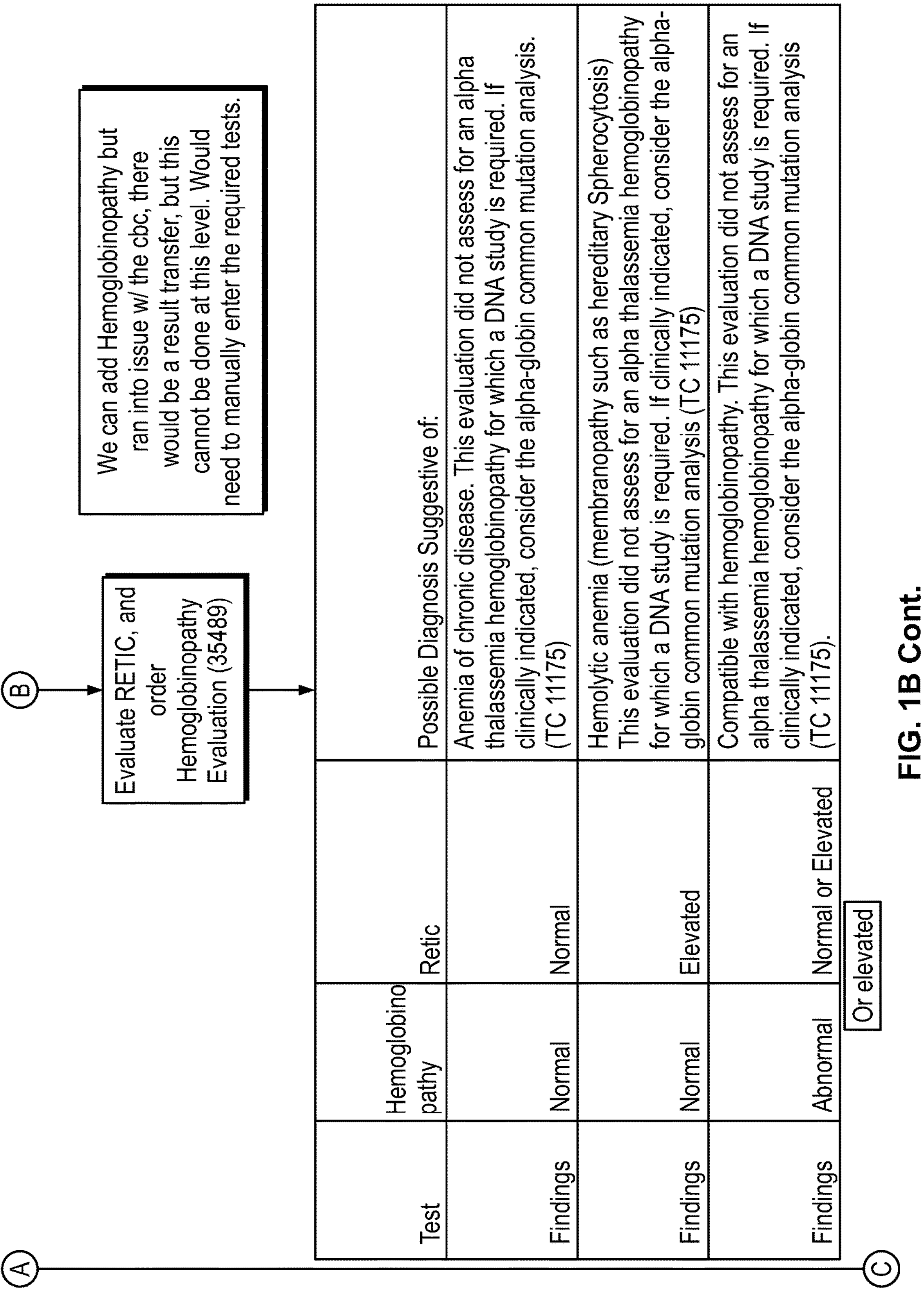

| Test | Hemoglobinopathy | Retic | Possible Diagnosis Suggestive of: |
|---|---|---|---|
| Findings | Normal | Normal | Anemia of chronic disease. This evaluation did not assess for an alpha thalassemia hemoglobinopathy for which a DNA study is required. If clinically indicated, consider the alpha-globin common mutation analysis. (TC 11175) |
| Findings | Normal | Elevated | Hemolytic anemia (membranopathy such as hereditary Spherocytosis) This evaluation did not assess for an alpha thalassemia hemoglobinopathy for which a DNA study is required. If clinically indicated, consider the alpha-globin common mutation analysis (TC 11175) |
| Findings | Abnormal | Normal or Elevated | Compatible with hemoglobinopathy. This evaluation did not assess for an alpha thalassemia hemoglobinopathy for which a DNA study is required. If clinically indicated, consider the alpha-globin common mutation analysis (TC 11175). |

FIG. 1B Cont.

SYSTEM FOR DETERMINING AN UNDERLYING CAUSE OF ANEMIA

CROSS-REFERENCE TO RELATED PATENT APPLICATIONS

The present application is the U.S. National Stage of PCT/US2021/017481, filed Feb. 10, 2021, which claims the benefit of and priority to U.S. Provisional Patent Application No. 62/972,835 filed on Feb. 11, 2020, the entire disclosure of which is incorporated by reference herein.

BACKGROUND

Anemia is the most common blood disorder in the United States, affecting more than three million people annually. Anemia is independently associated with poorer health outcomes in people with chronic diseases, with increased risks of developing heart and liver diseases. Risk for anemic conditions can be associated with an imbalanced diet, intestinal disorders, pregnancy, menstruation, blood diseases, autoimmune disorders, alcoholism, toxic chemical exposure, chronic conditions, or genetic predisposition.

SUMMARY

Disclosed herein are processes and systems for determining an underlying cause of anemia. In some embodiments, also disclosed herein are processes and systems for determining an underlying cause of microcytic anemia, normocytic anemia, and macrocytic anemia. In some embodiments, disclosed herein are methods of treating the underlying cause.

In one aspect, the present disclosure provides automated processes, which comprise determining from a blood sample obtained from an individual suspected of having anemia, by a processing module, a hemoglobin level, mean corpuscular hemoglobin concentration (MCHC), and mean corpuscular volume (MCV); comparing the hemoglobin level, MCHC level, and MCV value to a defined standard for hemoglobin level, MCHC, and MCV; and (i) assessing reticulocyte count, by the same processing module or by an additional processing module, if the MCHC level is elevated compared to the defined standard for MCHC; or (ii) assessing reticulocyte count, ferritin level, and hemoglobinopathy evaluation, by the same processing module and/or at least an additional processing module, if the hemoglobin level is lower than the defined standard for hemoglobin level, the MCV value is lower than the defined standard for MCV, and the MCHC level is normal or lower than the defined standard for MCHC; or (iii) assessing reticulocyte count, ferritin level, C-reactive protein (CRP), and comprehensive metabolic panel (CMP), by the same processing module and/or at least an additional processing module, if the hemoglobin level is lower than the defined standard for hemoglobin level, the MCV value is normal compared to the defined standard for MCV, and the MCHC level is normal or lower than the defined standard for MCHC; or (iv) assessing reticulocyte count, folate, vitamin B12, and hepatic function panel, by the same processing module and/or at least an additional processing module, if the hemoglobin level is lower than the defined standard for hemoglobin level, and the MCV value is elevated by at least about 10% compared to the defined standard for MCV.

In one aspect, the present disclosure provides automated processes for determining the cause of anemia comprising;

(a) assessing in a blood sample from an individual with anemia mean corpuscular hemoglobin concentration (MCHC) of the sample and comparing the MCHC level in the sample to a defined standard for MCHC;

(b-i) if the MCHC level in the sample in (a) is elevated compared to the defined standard for MCHC, assessing reticulocyte count of the sample and comparing the reticulocyte count of the sample to a defined standard reticulocyte count;

(c) if the reticulocyte count of the sample in (b-i) is normal or elevated compared to the defined standard reticulocyte count, recommending genetic testing of a hemolytic anemia condition;

(b-ii) if the MCHC level in the sample in (a) is not elevated compared to the defined standard for MCHC or if the reticulocyte count of the sample in (b-i) is low compared to the defined standard reticulocyte count, assessing hemoglobin level in the sample and comparing the hemoglobin level in the sample to a defined cutoff for hemoglobin;

(d-i) if the hemoglobin level in the sample in (b-ii) is not lower than the defined cutoff for hemoglobin, recommending no further testing;

(d-ii) if the hemoglobin level in the sample in (b-ii) is lower than the defined cutoff for hemoglobin, assessing reticulocyte count of the sample and comparing the reticulocyte count of the sample to a defined standard reticulocyte count, and assessing mean corpuscular volume (MCV) and comparing the MCV of the sample to a defined standard for MCV;

(e-i) if the MCV in the sample in (d-ii) is low compared to the defined standard for MCV, assessing ferritin level in the sample and comparing the ferritin level to a defined cutoff for ferritin;

(f-i) if the ferritin level in (e-i) is low compared to the defined cutoff for ferritin, suggesting the individual is iron deficient or recommending further testing of an alpha thalassemia hemoglobinopathy;

(f-ii) if the ferritin level in (e-i) is normal or high compared to the defined cutoff for ferritin, assessing reticulocyte count of the sample and comparing the reticulocyte count of the sample to a defined standard reticulocyte count and performing a hemoglobinopathy evaluation;

(g-i) if the reticulocyte count in (f-ii) is not elevated and the hemoglobinopathy evaluation is normal, suggesting the individual has anemia of a chronic disease;

(g-ii) if the reticulocyte count in (f-ii) is elevated and the hemoglobinopathy evaluation is normal, suggesting the individual has a hemolytic anemia; and (g-iii) if the reticulocyte count in (f-ii) is normal or elevated and the hemoglobinopathy evaluation is abnormal, suggesting the individual has anemia of a hemoglobinopathy;

(e-ii) if the MCV in the sample in (d-ii) is elevated by at least 10% compared to the defined standard for MCV, assessing B12 and/or folate levels in the sample and comparing the B12 and/or folate levels to a defined cutoffs for B12 and/or folate;

(h-i) if the B12 and/or folate levels in the sample in (e-ii) are lower than the defined cutoffs for B12 and/or folate, assessing methylmalonic acid content of the sample to confirm or exclude a B12 and/or folate deficiency;

(h-ii) if the B12 and/or folate levels in the sample in (e-ii) are higher than the defined cutoffs for B12 and/or folate, assessing reticulocyte count of the sample and comparing the reticulocyte count of the sample to a defined standard reticulocyte count;

(i-i) if the reticulocyte count of the sample in (h-ii) is normal or elevated compared to the defined standard reticulocyte count, recommending genetic testing of a hemolytic anemia condition;

(i-ii) if the reticulocyte count of the sample in (h-ii) is low compared to the defined standard reticulocyte count, assessing one or more markers of liver function in the sample and comparing the one or more markers of liver function in the sample to a defined range for the one or more markers of liver function;

(j-i) if the one or more markers of liver function in (i-ii) are within the defined range for the one or more markers of liver function, suggesting that the individual is assessed for a hematological disease; and (j-ii) if the one or more markers of liver function in (i-ii) are within the defined range for the one or more markers of liver function, suggesting that the individual is assessed for chronic disease secondary to liver disease with or without alcohol.

(e-iii) if the MCV in the sample in (d-ii) is normal compared to the defined standard for MCV, assessing ferritin level in the sample and comparing the ferritin level to a defined cutoff for ferritin;

(k-i) if the ferritin level in (e-iii) is low compared to the defined cutoff for ferritin, suggesting the individual is iron deficient and recommending further evaluation of iron deficiency;

(k-ii) if the ferritin level in (e-iii) is high compared to the defined cutoff for ferritin, suggesting the individual is having an acute or chronic phase reaction and recommending further clinical evaluation;

(k-iii) if the ferritin level in (e-iii) is normal compared to the defined cutoff for ferritin, assessing reticulocyte count of the sample and comparing the reticulocyte count of the sample to a defined standard reticulocyte count, and assessing C-reactive protein (CRP) level in the sample and comparing the CRP level in the sample to a defined cutoff for CRP;

(l-i) if the reticulocyte count and CRP in (k-iii) are normal, recommending further evaluation for chronic disease or dimorphic anemia (which is a combination of an iron deficiency and either a folic acid or B12 deficiency);

(l-ii) if the reticulocyte count in (k-iii) is increased and CRP in (l-iii) is normal, recommending further evaluation for hemolytic anemia or gastrointestinal bleeding;

(l-iii) if the reticulocyte count in (k-iii) is low or normal and the CRP in (l-iii) is increased, performing a complete metabolic panel (CMP), and if the CMP is abnormal, suggesting the individual has anemia of chronic disease.

In some embodiments, the hemolytic anemia condition for which genetic testing is recommended is hereditary xerocytosis (HX), sickle cell anemia, and/or hereditary spherocytosis.

In some embodiments, the defined cutoff for hemoglobin is about 13.2 mg/l for an adult male and about 11.7 mg/l for an adult female.

In some embodiments, the hemoglobinopathy evaluation comprises assessing hemoglobin A, hemoglobin F, total hemoglobin, hemoglobin A2 (Quant), hemoglobin S, hemoglobin C, hemoglobin E and any hemoglobin variants. In some embodiments, the hemoglobinopathy evaluation further comprises a red blood cell count, a hematocrit, assessing mean corpuscular volume (MCV), assessing mean corpuscular hemoglobin (MCH), and red blood cell distribution width (RDW).

In some embodiments, the hematological disease is myelodysplasia or a hematological malignancy.

In some embodiments, only a single blood sample is obtained from the individual. In some embodiments, the process is completed in 72 hours or less. In some embodiments, the individual is not under treatment for iron deficiency at the time of assessment. In some embodiments, the individual does not have a family history of red blood cell disorders. In some embodiments, the blood sample was obtained by or under the direction of a primary care physician.

In another aspect, the disclosure provides automated processes to determine the underlying cause of microcytic anemia comprising:

(a) determining the amount of ferritin in a blood sample from an individual with anemia and a mean corpuscular volume (MCV) is lower than a defined cutoff of about 80 fL or about 79 fL;

(i) if the ferritin level in is low compared to the defined cutoff for ferritin, suggesting the individual is iron deficient or recommending further testing of an alpha thalassemia hemoglobinopathy;

(ii) if the ferritin level in is normal or high compared to the defined cutoff for ferritin, assessing reticulocyte count of the sample and comparing the reticulocyte count of the sample to a defined standard reticulocyte count and performing a hemoglobinopathy evaluation;

(A) if the reticulocyte count in (ii) is not elevated and the hemoglobinopathy evaluation is normal, suggesting the individual has anemia of a chronic disease;

(B) if the reticulocyte count in (ii) is elevated and the hemoglobinopathy evaluation is normal, suggesting the individual has a hemolytic anemia; and (C) if the reticulocyte count in (ii) is normal or elevated and the hemoglobinopathy evaluation is abnormal, suggesting the individual has anemia of a hemoglobinopathy.

In some embodiments, the individual has low hemoglobin and a normal mean corpuscular hemoglobin concentration (MCHC).

In some embodiments, the hemoglobinopathy evaluation comprises assessing hemoglobin A, hemoglobin F, total hemoglobin, hemoglobin A2 (Quant), hemoglobin S, hemoglobin C, hemoglobin E and any hemoglobin variants. In some embodiments, the hemoglobinopathy evaluation further comprises a red blood cell count, a hematocrit, assessing mean corpuscular volume (MCV), assessing mean corpuscular hemoglobin (MCH), and red blood cell distribution width (RDW).

In some embodiments, only a single blood sample is obtained from the individual. In some embodiments, the process is completed in 72 hours or less.

In another aspect, the disclosure provides automated processes to determine the underlying cause of normocytic anemia comprising:

(a) determining the amount of ferritin in a blood sample from an individual with anemia and a mean corpuscular volume (MCV) is within the range of from about 80 fL to about 100 fL, from about 80 fL to about 98 fL, or from about 80 fL to about 96 fL;
  (i) if the ferritin level is low compared to the defined cutoff for ferritin, suggesting the individual is iron deficient (which may be caused by an acute or chronic phase reaction) and recommending further evaluation of iron deficiency;
  (ii) if the ferritin level is high compared to the defined cutoff for ferritin, suggesting the individual is having an acute phase reaction and recommending further clinical evaluation;
  (iii) if the ferritin level is normal compared to the defined cutoff for ferritin, assessing reticulocyte count of the sample and comparing the reticulocyte count of the sample to a defined standard reticulocyte count, and assessing C-reactive protein (CRP) level in the sample and comparing the CRP level in the sample to a defined cutoff for CRP;
    (A) if the reticulocyte count and CRP in (iii) are normal, recommending further evaluation for chronic disease or dimorphic anemia;
    (B) if the reticulocyte count in (iii) is increased and CRP in (l-iii) is normal, recommending further evaluation for hemolytic anemia or gastrointestinal bleeding;
    (C) if the reticulocyte count in (iii) is low or normal and the CRP in (l-iii) is increased, performing a complete metabolic panel (CMP), and if the CMP is abnormal, suggesting the individual has anemia of chronic disease.

In some embodiments, the individual has low hemoglobin and a normal mean corpuscular hemoglobin concentration (MCHC).

In some embodiments, only a single blood sample is obtained from the individual. In some embodiments, the process is completed in 72 hours or less.

In another aspect, the disclosure provides automated processes to determine the underlying cause of macrocytic anemia comprising:

(a) determining the amount of B12 and/or folate in a blood sample from an individual with anemia and a mean corpuscular volume (MCV) is at least 10% more than a defined cutoff of about 96 fL, about 97 fL, about 98 fL, about 99 fL, or about 100 fL;
  (i) if the B12 and/or folate levels in the sample in are lower than defined cutoffs for B12 and/or folate, assessing methylmalonic acid content of the sample to confirm or exclude a B12 and/or folate deficiency;
  (ii) if the B12 and/or folate levels in the sample in are higher than the defined cutoffs for B12 and/or folate, assessing reticulocyte count of the sample and comparing the reticulocyte count of the sample to a defined standard reticulocyte count;
    (A) if the reticulocyte count of the sample in (ii) is normal or elevated compared to the defined standard reticulocyte count, recommending genetic testing of a hemolytic anemia condition;
    (B) if the reticulocyte count of the sample in (ii) is low compared to the defined standard reticulocyte count, assessing one or more markers of liver function in the sample and comparing the one or more markers of liver function in the sample to a defined range for the one or more markers of liver function;
      (I) if the one or more markers of liver function in (B) are within the defined range for the one or more markers of liver function, suggesting that the individual is assessed for a hematological disease; and
      (II) if the one or more markers of liver function in (B) are within the defined range for the one or more markers of liver function, suggesting that the individual is assessed for chronic disease secondary to liver disease with or without alcohol.

In some embodiments, the individual has low hemoglobin and a normal mean corpuscular hemoglobin concentration (MCHC). In some embodiments, the hemolytic anemia condition for which genetic testing is recommended is hereditary xerocytosis (HX), sickle cell anemia, and/or hereditary spherocytosis.

In some embodiments, only a single blood sample is obtained from the individual. In some embodiments, the process is completed in 72 hours or less.

In another aspect, the disclosure provides automated processes for determining an underlying cause of anemia, comprising:

determining from a blood sample obtained from an individual suspected of having anemia, by a processing module, a hemoglobin level, mean corpuscular hemoglobin concentration (MCHC), and mean corpuscular volume (MCV);

comparing the hemoglobin level, MCHC level, and MCV value to a defined standard for hemoglobin level, MCHC, and MCV; and assessing reticulocyte count, by the same processing module or by an additional processing module, if the MCHC level is elevated compared to the defined standard for MCHC; or assessing reticulocyte count, ferritin level, and hemoglobinopathy evaluation, by the same processing module and/or at least an additional processing module, if the hemoglobin level is lower than the defined standard for hemoglobin level, the MCV value is lower than the defined standard for MCV, and the MCHC level is normal or lower than the defined standard for MCHC; or assessing reticulocyte count, ferritin level, C-reactive protein (CRP), and comprehensive metabolic panel (CMP), by the same processing module and/or at least an additional processing module, if the hemoglobin level is lower than the defined standard for hemoglobin level, the MCV value is normal compared to the defined standard for MCV, and the MCHC level is normal or lower than the defined standard for MCHC; or assessing reticulocyte count, folate, vitamin B12, and hepatic function panel, by the same processing module and/or at least an additional processing module, if the hemoglobin level is lower than the defined standard for hemoglobin level, and the MCV value is elevated by at least about 10% compared to the defined standard for MCV.

Some embodiments may further comprise comparing the reticulocyte count of step i) with a defined standard, wherein an elevated reticulocyte count is indicative of hemolytic anemia or may be due to a gastrointestinal (GI) bleed.

Some embodiments may further comprise comparing the ferritin level of step ii) with a defined standard, wherein a reduced level of ferritin is indicative of iron deficiency.

Some embodiments may further comprise comparing the reticulocyte count, ferritin level, and hemoglobinopathy evaluation of step ii) with their respective defined standards, wherein:

a) a normal or elevated level of ferritin, a normal hemoglobinopathy evaluation and a normal reticulocyte count are indicative of anemia of chronic disease;

b) a normal or elevated level of ferritin, a normal hemoglobinopathy evaluation, and an elevated reticulocyte count are indicative of hemolytic anemia; or c) a normal or elevated level of ferritin, an abnormal hemoglobinopathy evaluation, and a normal or elevated reticulocyte count are indicative of anemia of a hemoglobinopathy.

Some embodiments may further comprise comparing the ferritin level of step iii) with a defined standard, wherein a reduced level of ferritin is indicative of iron deficiency, optionally early iron deficiency.

Some embodiments may further comprise comparing the ferritin level of step iii) with a defined standard, wherein an elevated level of ferritin is indicative of an acute phase reaction or a chronic phase reaction.

Some embodiments may further comprise comparing the ferritin level, CRP, CMP, and the reticulocyte count of step iii) with their respective defined standards, wherein:

a) a normal level of ferritin and an elevated reticulocyte count are indicative of hemolytic anemia or gastrointestinal bleeding;

b) a normal level of ferritin, a low or normal reticulocyte count, an elevated level of CRP, and an abnormal or normal CMP are indicative of anemia of chronic disease (ACD); or c) a normal level of ferritin, a normal reticulocyte count, and a normal level of CRP are indicative of chronic disease or dimorphic anemia.

Some embodiments may further comprise comparing folate and vitamin B12 of step iv) with their respective defined standards, wherein either a low level of folate or vitamin B12 is indicative of folate or vitamin B12 deficiency.

Some embodiments may further comprise comparing the reticulocyte count, folate, and vitamin B12 of step iv) with their respective defined standards, wherein either a low level of folate or vitamin B12 and an elevated reticulocyte count are indicative of hemolytic anemia.

Some embodiments may further comprise comparing the reticulocyte count, folate, vitamin B12, and the hepatic function panel of step iv) with their respective defined standards, wherein:

a) either a low level of folate or vitamin B12, an elevated reticulocyte count, and a normal hepatic function are indicative of a hematologic disease; or b) either a low level of folate or vitamin B12, an elevated reticulocyte count, and an abnormal hepatic function are indicative of anemia of chronic disease, optionally secondary to a liver disease, further optionally associated with alcohol.

In some embodiments, the hemolytic anemia comprises an inherited hemolytic anemia or an acquired hemolytic anemia. In some embodiments, the inherited hemolytic anemia comprises sickle cell anemia, thalassemias, hereditary xerocytosis, hereditary spherocytosis, hereditary elliptocytosis (ovalocytosis), glucose-6-phosphate dehydrogenase (G6PD) deficiency, and pyruvate kinase deficiency. In some embodiments, the acquired hemolytic anemia comprises immune hemolytic anemia, mechanical hemolytic anemias, paroxysmal nocturnal hemoglobinuria, pathogen-induced acquired hemolytic anemia, and chemical-induced acquired hemolytic anemia. In some embodiments, the immune hemolytic anemia comprises autoimmune hemolytic anemia (AIHA), alloimmune hemolytic anemia, and drug-induced hemolytic anemia. In some embodiments, the pathogen-induced acquired hemolytic anemia comprises one or more pathogens that damage red blood cells, optionally comprising protozoans from the genus *Plasmodium* or bacteria from the genus *Borrelia*. In some embodiments, the *Plasmodium* comprises *P. falciparum, P. malariae, P. ovale*, and *P. vivax*. In some embodiments, *Borrelia* comprises *B. burgdorferi, B. mayonii, B. afzelii*, and *B. garinii*. In some embodiments, the chemical-induced acquired hemolytic anemia comprises one or more chemicals that damage red blood cells, optionally comprising toxic chemicals or venom. In some embodiments, the hematologic disease comprises myelodysplasia.

Some embodiments may further comprise a methylmelonic acid test.

In some embodiments of any of the foregoing aspects, a defined standard for MCHC is from about 32% to about 36%, from about 33% to about 36%, from about 33% to about 35%, or from about 32% to about 35%.

In some embodiments of any of the foregoing aspects, an elevated MCHC level is greater than about 35% or greater than about 36%.

In some embodiments of any of the foregoing aspects, a decreased or low MCHC level is less than about 33% or less than about 32%.

In some embodiments of any of the foregoing aspects, a defined standard for MCHC is from about 32 g/dL to about 36 g/dL, from about 33 g/dL to about 36 g/dL, or from about 33.4 g/dL to about 35.5 g/dL.

In some embodiments of any of the foregoing aspects, an elevated MCHC level is greater than about 35 g/dL, greater than about 35.5 g/dL, or greater than about 36 g/dL.

The automated process of any of the foregoing aspects, wherein a decreased or low MCHC level is less than about 33.4 g/dL, less than about 33 g/dL, or less than about 32 g/dL.

In some embodiments of any of the foregoing aspects, a defined standard for hemoglobin level for men is from about 13 mg/L to about 17.5 mg/L or from about 13.2 mg/L to about 17.5 mg/L.

In some embodiments of any of the foregoing aspects, a decreased hemoglobin level for men is less than about 13.2 mg/L or less than about 13 mg/L.

In some embodiments of any of the foregoing aspects, a defined standard for hemoglobin level for women is from about 11 mg/L to about 15.3 mg/L, from about 11.6 mg/L to about 15 mg/L, from about 11.7 mg/L to about 15 mg/L, or from about 12 mg/L to about 15 mg/L.

In some embodiments of any of the foregoing aspects, a decreased hemoglobin level for women is less than about 11 mg/L, less than about 11.6 mg/L, less than about 11.7 mg/L, or less than about 12 mg/L.

In some embodiments of any of the foregoing aspects, a defined standard for MCV is from about 80 fL to about 100 fL, from about 80 fL to about 98 fL, or from about 80 fL to about 96 fL.

In some embodiments of any of the foregoing aspects, an elevated MCV value is greater than about 96 fL, greater than about 97 fL, greater than about 98 fL, greater than about 99 fL, or greater than 100 fL.

In some embodiments of any of the foregoing aspects, a reduced or low MCV value is less than about 80 fL or less than about 79 fL.

In some embodiments of any of the foregoing aspects, a defined standard for the reticulocyte count is from about 0.5% to about 2.5%, from about 0.5% to about 2%, or from about 0.5% to about 1.5%.

In some embodiments of any of the foregoing aspects, an elevated reticulocyte count is greater than 1.5%, greater than 2%, or greater than 2.5%.

In some embodiments of any of the foregoing aspects, a defined standard for the reticulocyte count is from about $10\times10^9$ to about $110\times10^9$ RBCs/L, from about $50\times10^9$ to about $100\times10^9$ RBCs/L, or from about $50\times10^9$ to about $150\times10^9$ RBCs/L.

In some embodiments of any of the foregoing aspects, an elevated reticulocyte count is greater than $100\times10^9$ RBCs/L, greater than $110\times10^9$ RBCs/L, or greater than $150\times10^9$ RBCs/L.

In some embodiments of any of the foregoing aspects, a defined standard for ferritin for men is from about 12 to about 300 ng/mL, from about 20 to about 300 ng/mL, or from about 20 to about 250 ng/mL.

In some embodiments of any of the foregoing aspects, an elevated level of ferritin for men is greater than about 250 ng/mL or greater than about 300 ng/mL.

In some embodiments of any of the foregoing aspects, a defined standard for ferritin for women is from about 12 to about 270 ng/mL, from about 12 to about 263 ng/mL, from about 20 to about 200 ng/mL, from about 12 to about 150 ng/mL, or from about 10 to about 120 ng/mL.

In some embodiments of any of the foregoing aspects, an elevated level of ferritin for women is greater than about 120 ng/mL, greater than about 150 ng/mL, greater than about 200 ng/mL, greater than about 263 ng/mL, or greater than about 270 ng/mL.

In some embodiments of any of the foregoing aspects, a decreased or low level of ferritin is less than about 20 ng/mL, less than about 12 ng/mL, or less than 10 ng/mL.

In some embodiments of any of the foregoing aspects, a defined standard for CRP is from about 0.2 mg/L to about 6.1 mg/L, from about 0.2 mg/L to about 6 mg/L, or from about 0.2 mg/L to about 5 mg/L.

In some embodiments of any of the foregoing aspects, an elevated CRP level is greater than about 5 mg/L, greater than about 6 mg/L, or greater than about 6.2 mg/L.

In some embodiments of any of the foregoing aspects, a defined standard for folate conducted on a blood plasma is from about 2 ng/mL to about 10 ng/mL or from about 2.7 ng/mL to about 17 ng/mL.

In some embodiments of any of the foregoing aspects, a defined standard for folate conducted on RBCs is from about 140 ng/mL to about 960 ng/mL.

In some embodiments of any of the foregoing aspects, a defined standard for vitamin B12 is from about 200 to about 900 ng/mL.

In some embodiments of any of the foregoing aspects, the hepatic function panel comprises testing the level of total protein, albumin, bilirubin, alkaline phosphatase (ALP), alanine transaminase (ALT), and aspartate aminotransferase (AST). In some embodiments, a defined standard for ALP is from about 25 IU/L to about 160 IU/L or from about 40 IU/L to about 129 IU/L. In some embodiments, a defined standard for ALT is from about 0 IU/L to about 55 IU/L or from about 7 IU/L to about 55 IU/L. In some embodiments, a defined standard for AST is from about 0 IU/L to about 40 IU/L or from about 8 IU/L to about 48 IU/L.

In some embodiments of any of the foregoing aspects, the hemoglobinopathy evaluation detects the presence of a hemoglobin variant and/or thalassemia. In some embodiments, the hemoglobin variant comprises hemoglobin A, hemoglobin A2, hemoglobin F, hemoglobin S, hemoglobin C, or hemoglobin E. In some embodiments, the hemoglobinopathy evaluation does not detect the presence of α-thalassemia.

In some embodiments of any of the foregoing aspects, the process does not comprise a blood smear test.

In some embodiments of any of the foregoing aspects, the process does not detect and/or assess red cell distribution width (RWD).

In some embodiments of any of the foregoing aspects, the process comprises carrying out a complete blood count (CBC) test to detect the hemoglobin level, MCHC, and MCV.

In some embodiments of any of the foregoing aspects, the process is completed in about 72 hours or less. In some embodiments of any of the foregoing aspects, the individual is not under a treatment for iron deficiency. In some embodiments of any of the foregoing aspects, a single blood sample is obtained from the individual.

In some embodiments of any of the foregoing aspects, the comparing step is carried out by a processor.

In another aspect, the disclosure provides methods of treating an underlying cause of anemia in an individual in need thereof, comprising:

assessing a hemoglobin level, mean corpuscular hemoglobin concentration (MCHC), and mean corpuscular volume (MCV) from a blood sample obtained from the individual;

comparing the hemoglobin level, MCHC level, and MCV value to a defined standard for hemoglobin level, MCHC, and MCV;

carrying out one or more additional tests selected from:

a reticulocyte count if the MCHC level is elevated compared to the defined standard for MCHC;

a reticulocyte count, ferritin level, and hemoglobinopathy evaluation if the hemoglobin level is lower than the defined standard for hemoglobin level, the MCV value is lower than the defined standard for MCV, and the MCHC level is normal or lower than the defined standard for MCHC;

a reticulocyte count, ferritin level, C-reactive protein (CRP), and comprehensive metabolic panel (CMP) if the hemoglobin level is lower than the defined standard for hemoglobin level, the MCV value is normal compared to the defined standard for MCV, and the MCHC level is normal or lower than the defined standard for MCHC; or a reticulocyte count, folate, vitamin B12, and hepatic function panel if the hemoglobin level is lower than the defined standard for hemoglobin level, and the MCV value is elevated by at least about 10% compared to the defined standard for MCV; and administering a treatment to the individual, thereby treating the underlying cause of anemia.

Some embodiments may further comprise comparing the reticulocyte count with a defined standard, wherein an elevated reticulocyte count is indicative of hemolytic anemia.

Some embodiments may further comprise comparing the ferritin level with a defined standard, wherein a reduced level of ferritin is indicative of iron deficiency.

Some embodiments may further comprise comprises comparing the reticulocyte count, ferritin level, and hemoglobinopathy evaluation with their respective defined standards, wherein:

a) a normal or elevated level of ferritin, a normal hemoglobinopathy evaluation and a normal reticulocyte count are indicative of anemia of chronic disease;

b) a normal or elevated level of ferritin, a normal hemoglobinopathy evaluation, and an elevated reticulocyte count are indicative of hemolytic anemia; or c) a normal or elevated level of ferritin, an abnormal hemoglobinopathy evaluation, and a normal or elevated reticulocyte count are indicative of anemia of a hemoglobinopathy.

Some embodiments may further comprise comparing the ferritin level with a defined standard, wherein a reduced level of ferritin is indicative of iron deficiency, optionally early iron deficiency.

Some embodiments may further comprise comparing the ferritin level with a defined standard, wherein an elevated level of ferritin is indicative of an acute phase reaction.

Some embodiments may further comprise comparing the ferritin level, CRP, CMP, and the reticulocyte count with their respective defined standards, wherein:

a) a normal level of ferritin and an elevated reticulocyte count are indicative of hemolytic anemia or gastrointestinal bleeding;

b) a normal level of ferritin, a low or normal reticulocyte count, an elevated level of CRP, and an abnormal or normal CMP are indicative of anemia of chronic disease (ACD); or c) a normal level of ferritin, a normal reticulocyte count, and a normal level of CRP are indicative of a chronic disease or dimorphic anemia.

Some embodiments may further comprise comparing folate and vitamin B12 with their respective defined standards, wherein either a low level of folate or vitamin B12 is indicative of folate or vitamin B12 deficiency.

Some embodiments may further comprise comparing the reticulocyte count, folate, and vitamin B12 with their respective defined standards, wherein either a low level of folate or vitamin B12 and an elevated reticulocyte count are indicative of hemolytic anemia.

Some embodiments may further comprise comparing the reticulocyte count, folate, vitamin B12, and the hepatic function panel with their respective defined standards, wherein:

a) either a low level of folate or vitamin B12, an elevated reticulocyte count, and a normal hepatic function are indicative of a hematologic disease; or b) either a low level of folate or vitamin B12, an elevated reticulocyte count, and an abnormal hepatic function are indicative of anemia of chronic disease, optionally secondary to a liver disease, further optionally associated with alcohol.

Some embodiments may further comprise a methylmelonic acid test.

Some embodiments may further comprise a genetic testing.

In some embodiments, the hemolytic anemia comprises an inherited hemolytic anemia or an acquired hemolytic anemia. For example, in some embodiments, the inherited hemolytic anemia comprises sickle cell anemia, thalassemia, hereditary xerocytosis, hereditary spherocytosis, hereditary elliptocytosis (ovalocytosis), glucose-6-phosphate dehydrogenase (G6PD) deficiency, and pyruvate kinase deficiency. In some embodiments, the acquired hemolytic anemia comprises immune hemolytic anemia, mechanical hemolytic anemias, paroxysmal nocturnal hemoglobinuria, pathogen-induced acquired hemolytic anemia, and chemical-induced acquired hemolytic anemia. In some embodiments, the immune hemolytic anemia comprises autoimmune hemolytic anemia (AIHA), alloimmune hemolytic anemia, and drug-induced hemolytic anemia. In some embodiments, the pathogen-induced acquired hemolytic anemia comprises one or more pathogens that damage red blood cells, optionally comprising protozoans from the genus *Plasmodium* or bacteria from the genus *Borrelia*. In some embodiments, *Plasmodium* comprises *P. falciparum, P. malariae, P. ovale*, and *P. vivax*. In some embodiments, *Borrelia* comprises *B. burgdorferi, B. mayonii, B. afzelii*, and *B. garinii*. In some embodiments, the chemical-induced acquired hemolytic anemia comprises one or more chemicals that damage red blood cells, optionally comprising toxic chemicals or venom.

In some embodiments, the hematologic disease comprises myelodysplasia.

In some embodiments, a treatment for hemolytic anemia comprises blood transfusion, plasmapheresis, blood and/or marrow stem cell transplant, surgery, a therapeutic agent, or a combination thereof. In some embodiments, a treatment for iron deficiency anemia (IDA) comprises administration of soluble iron. In some embodiments, a treatment for anemia of chronic disease (ACD) comprises a steroid or a nonsteroidal anti-inflammatory agent for the treatment of an underlying inflammation, antibiotics for an underlying pathogenic infection, or a cancer treatment.

In some embodiments, a defined standard for MCHC is from about 32% to about 36%, from about 33% to about 36%, from about 33% to about 35%, or from about 32% to about 35%. In some embodiments, an elevated MCHC level is greater than about 35% or greater than about 36%. In some embodiments, a decreased or low MCHC level is less than about 33% or less than about 32%. In some embodiments, a defined standard for MCHC is from about 32 g/dL to about 36 g/dL, from about 33 g/dL to about 36 g/dL, or from about 33.4 g/dL to about 35.5 g/dL. In some embodiments, an elevated MCHC level is greater than about 35 g/dL, greater than about 35.5 g/dL, or greater than about 36 g/dL. In some embodiments, a decreased or low MCHC level is less than about 33.4 g/dL, less than about 33 g/dL, or less than about 32 g/dL.

In some embodiments, a defined standard for hemoglobin level for men is from about 13 mg/L to about 17.5 mg/L or from about 13.2 mg/L to about 17.5 mg/L. In some embodiments, a decreased hemoglobin level for men is less than about 13.2 mg/L or less than about 13 mg/L. In some embodiments, a defined standard for hemoglobin level for women is from about 11 mg/L to about 15.3 mg/L, from about 11.6 mg/L to about 15 mg/L, from about 11.7 mg/L to about 15 mg/L, or from about 12 mg/L to about 15 mg/L. In some embodiments, a decreased hemoglobin level for women is less than about 11 mg/L, less than about 11.6 mg/L, less than about 11.7 mg/L, or less than about 12 mg/L.

In some embodiments, a defined standard for MCV is from about 80 fL to about 100 fL, from about 80 fL to about 98 fL, or from about 80 fL to about 96 fL. In some embodiments, an elevated MCV value is greater than about 96 fL, greater than about 97 fL, greater than about 98 fL, greater than about 99 fL, or greater than 100 fL. In some embodiments, a reduced or low MCV value is less than about 80 fL or less than about 79 fL.

In some embodiments, a defined standard for the reticulocyte count is from about 0.5% to about 2.5%, from about 0.5% to about 2%, or from about 0.5% to about 1.5%.

In some embodiments, an elevated reticulocyte count is greater than 1.5%, greater than 2%, or greater than 2.5%.

In some embodiments, a defined standard for the reticulocyte count is from about $10\times10^9$ to about $110\times10^9$ RBCs/L, from about $50\times10^9$ to about $100\times10^9$ RBCs/L, or from about $50\times10^9$ to about $150\times10^9$ RBCs/L.

In some embodiments, an elevated reticulocyte count is greater than $100\times10^9$ RBCs/L, greater than $110\times10^9$ RBCs/L, or greater than $150\times10^9$ RBCs/L.

In some embodiments, a defined standard for ferritin for men is from about 12 to about 300 ng/mL, from about 20 to about 300 ng/mL, or from about 20 to about 250 ng/mL.

In some embodiments, an elevated level of ferritin for men is greater than about 250 ng/mL or greater than about 300 ng/mL.

In some embodiments, a defined standard for ferritin for women is from about 12 to about 270 ng/mL, from about 12 to about 263 ng/mL, from about 20 to about 200 ng/mL, from about 12 to about 150 ng/mL, or from about 10 to about 120 ng/mL.

In some embodiments, an elevated level of ferritin for women is greater than about 120 ng/mL, greater than about 150 ng/mL, greater than about 200 ng/mL, greater than about 263 ng/mL, or greater than about 270 ng/mL.

In some embodiments, a decreased or low level of ferritin is less than about 20 ng/mL, less than about 12 ng/mL, or less than 10 ng/mL.

In some embodiments, a defined standard for CRP is from about 0.2 mg/L to about 6.1 mg/L, from about 0.2 mg/L to about 6 mg/L, or from about 0.2 mg/L to about 5 mg/L.

In some embodiments, an elevated CRP level is greater than about 5 mg/L, greater than about 6 mg/L, or greater than about 6.2 mg/L.

In some embodiments, a defined standard for folate conducted on a blood plasma is from about 2 ng/mL to about 10 ng/mL or from about 2.7 ng/mL to about 17 ng/mL.

In some embodiments, a defined standard for folate conducted on RBCs is from about 140 ng/mL to about 960 ng/mL.

In some embodiments, a defined standard for vitamin B12 is from about 200 to about 900 ng/mL.

In some embodiments, the hepatic function panel comprises testing the level of total protein, albumin, bilirubin, alkaline phosphatase (ALP), alanine transaminase (ALT), and aspartate aminotransferase (AST). In some embodiments, a defined standard for ALP is from about 25 IU/L to about 160 IU/L or from about 40 IU/L to about 129 IU/L. In some embodiments, a defined standard for ALT is from about 0 IU/L to about 55 IU/L or from about 7 IU/L to about 55 IU/L. In some embodiments, a defined standard for AST is from about 0 IU/L to about 40 IU/L or from about 8 IU/L to about 48 IU/L.

In another aspect, the present disclosure provides methods of treating an underlying cause of microcytic anemia in an individual in need thereof, comprising:

assessing a reticulocyte count, ferritin level, and a hemoglobinopathy evaluation from a blood sample obtained from the individual;

comparing the reticulocyte count and ferritin level with their respective defined standard; and administering to the individual a soluble form of iron if the ferritin level is lower than the defined standard; or administering to the individual a treatment for anemia of chronic disease if the level of ferritin is normal or elevated compared to the defined standard, the reticulocyte count is normal compared to the defined standard, and the hemoglobinopathy evaluation is normal; or administering to the individual a treatment for hemolytic anemia if the level of ferritin is normal or elevated compared to the defined standard, the reticulocyte count is elevated compared to the defined standard, and the hemoglobinopathy evaluation is normal; or administering to the individual a treatment for hemoglobinopathy if the level of ferritin is normal or elevated compared to the defined standard, the reticulocyte count is normal or elevated compared to the defined standard, and the hemoglobinopathy evaluation is abnormal.

In another aspect, the present disclosure provides methods of treating an underlying cause of normocytic anemia in an individual in need thereof, comprising:

assessing a reticulocyte count, ferritin level, C-reactive protein (CRP), and comprehensive metabolic panel (CMP) from a blood sample obtained from the individual;

comparing the reticulocyte count, ferritin level, CRP level, and CMP with their respective defined standard; and administering to the individual a soluble form of iron if the ferritin level is lower than the defined standard; or carrying out an additional evaluation of the individual if the ferritin level is elevated compared to the defined standard; or administering to the individual a treatment for hemolytic anemia or gastrointestinal bleeding if the ferritin level is normal compared to the defined standard and the reticulocyte count is elevated compared to the defined standard; or administering to the individual a treatment for anemia of chronic disease (ACD) if the ferritin level is normal compared to the defined standard, the reticulocyte count is elevated compared to the defined standard, and the CMP is normal or abnormal; or administering to the individual a treatment for a chronic disease or dimorphic anemia if the ferritin level is normal compared to the defined standard, the reticulocyte count is normal compared to the defined standard, and the CRP is normal.

In another aspect, the disclosure provides methods of treating an underlying cause of macrocytic anemia in an individual in need thereof, comprising:

assessing a reticulocyte count, folate, vitamin B12, and hepatic function panel from a blood sample obtained from the individual;

comparing the reticulocyte count, folate, vitamin B12, and hepatic function panel with their respective defined standard; and administering to the individual a folate supplement or a vitamin B12 supplement if either the level of folate or vitamin B12 is low compared to the defined standard; or administering to the individual a treatment for hemolytic anemia if the level of folate or vitamin B12 is low compared to the defined standard and the reticulocyte count is elevated compared to the defined standard; or administering to the individual a treatment for a hematologic disease if the level of folate or vitamin B12 is low compared to the defined standard, the reticulocyte count is elevated compared to the defined standard, and the hepatic function is normal compared to a defined standard; or administering to the individual a treatment for anemia of chronic disease if the level of folate or vitamin B12 is low compared to the defined standard, the reticulocyte count is elevated compared to the defined standard, and the hepatic function is abnormal compared to a defined standard.

The following detailed description is exemplary and explanatory, and is intended to provide further explanation of the invention.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

Figure 1A:
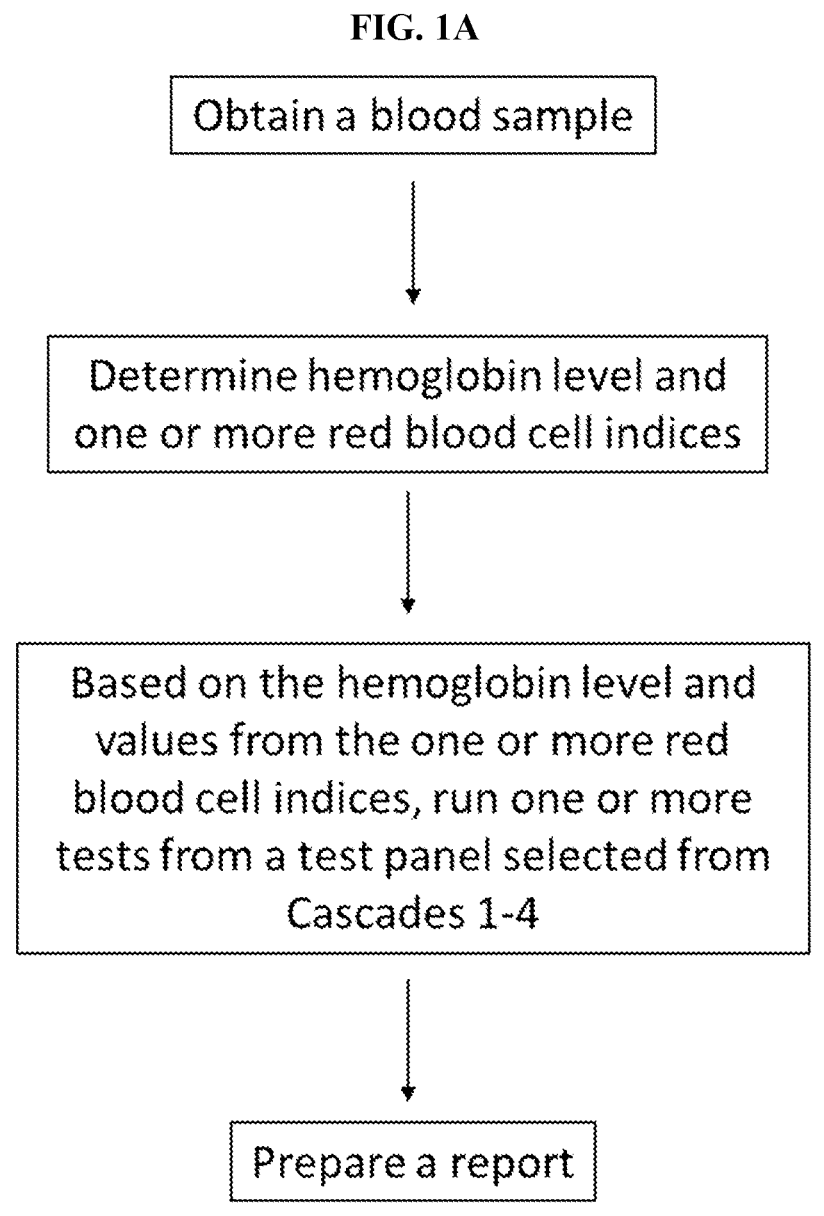

FIG. 1A and FIG. 1B illustrate an automated process described herein for determining an underlying cause of anemia.

DETAILED DESCRIPTION

Figure 1B:
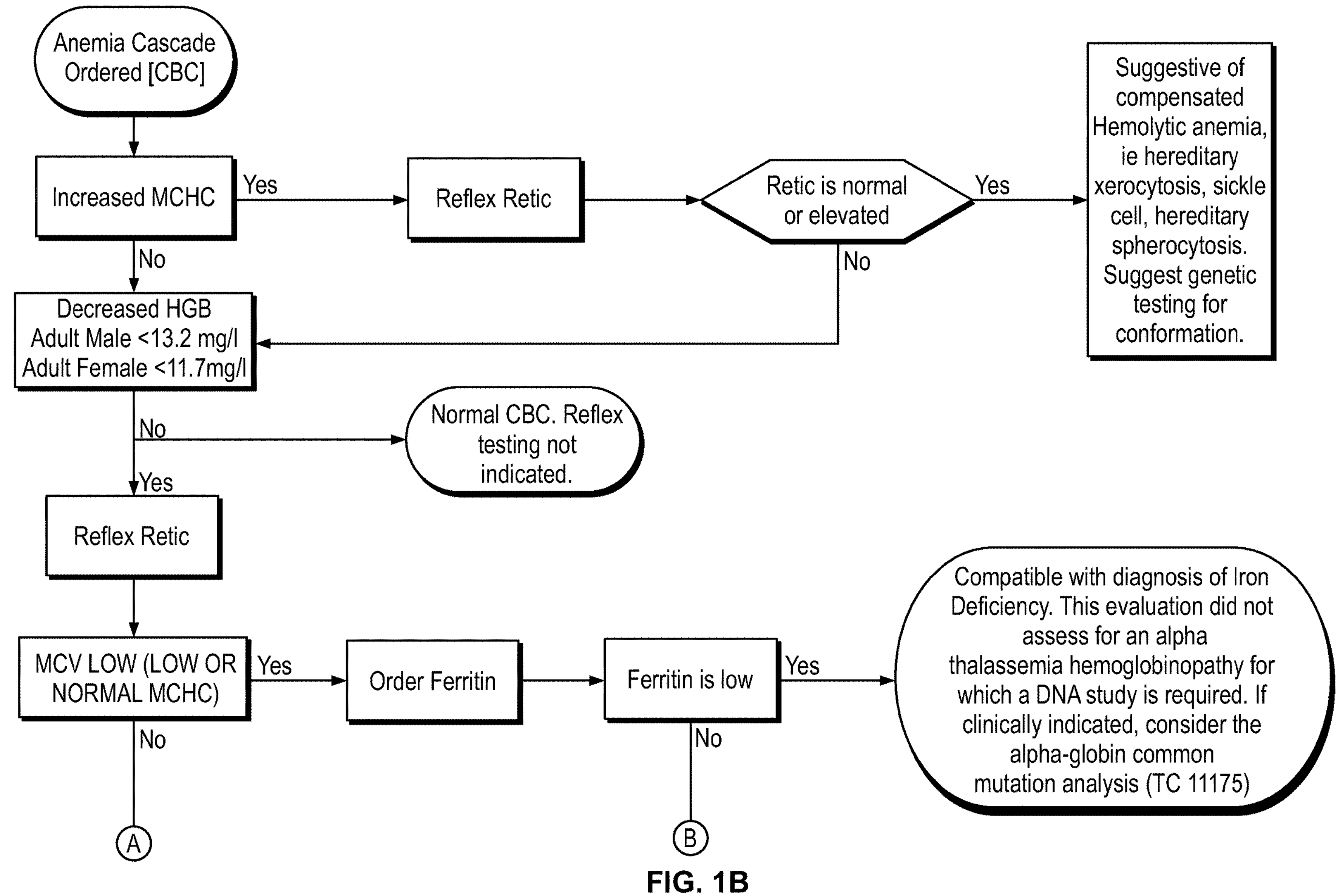
Figure 1B:
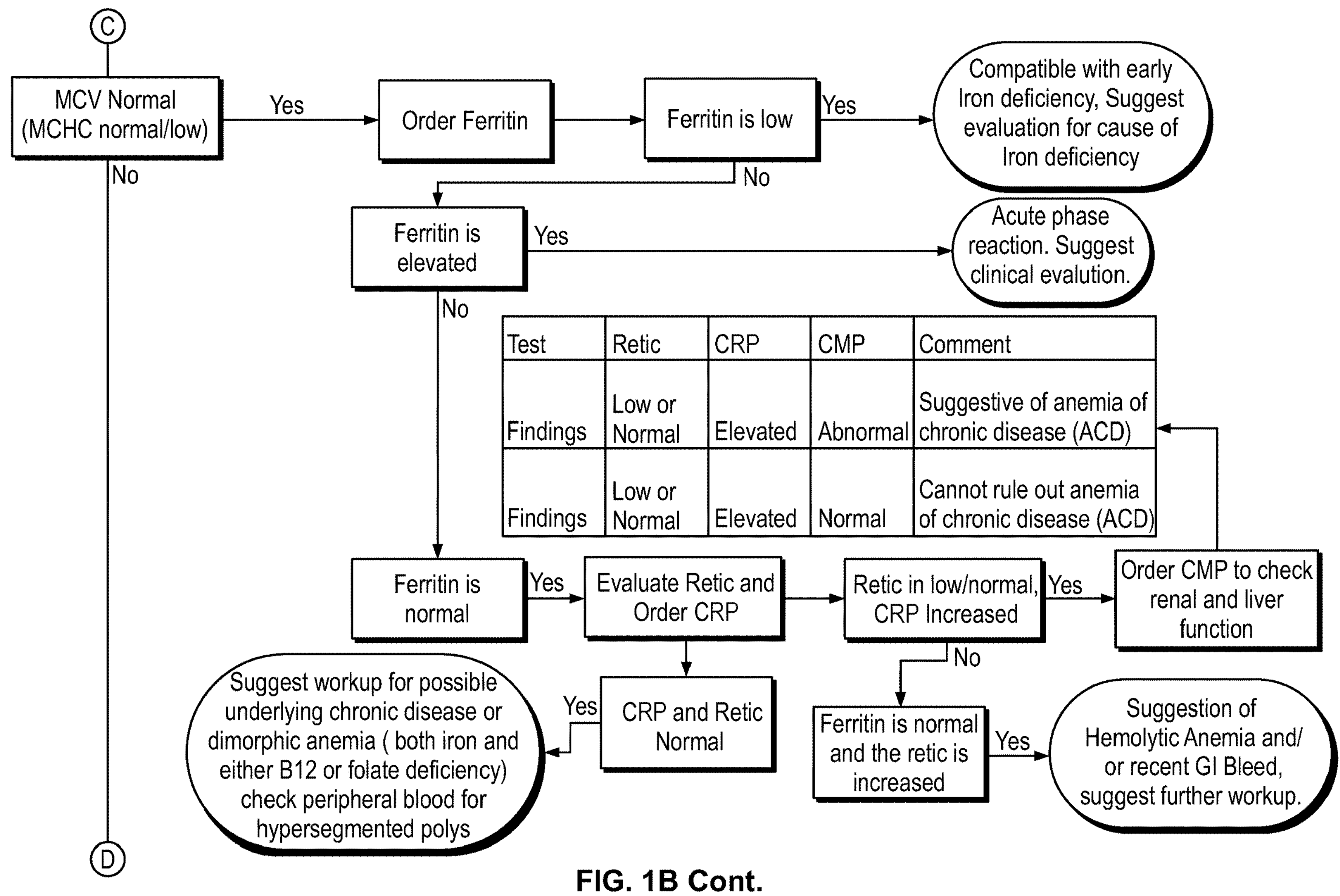
Figure 1B:
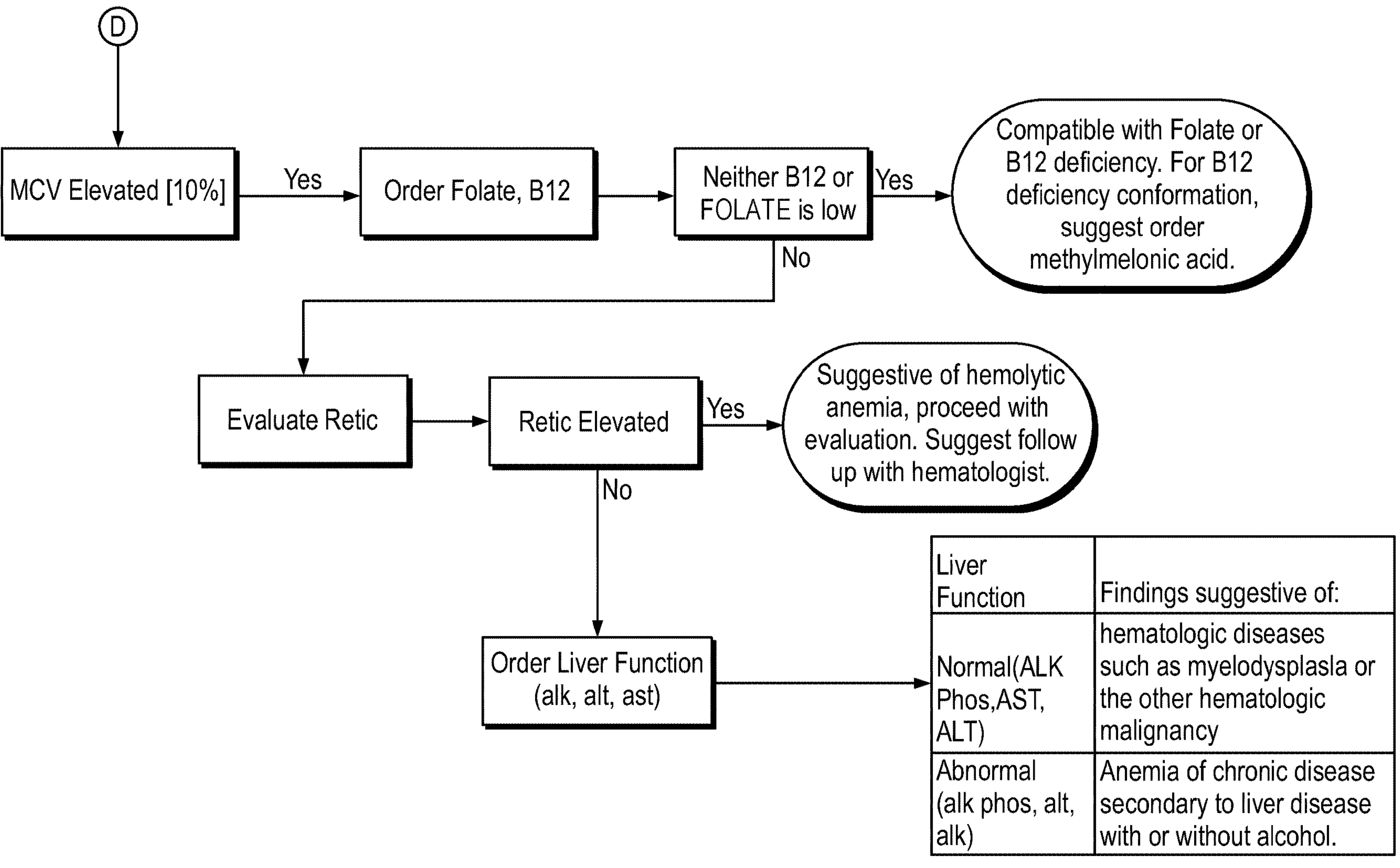

Anemia is a condition in which a number of red blood cells (RBCs) is insufficient to meet a body's physiological need. Anemia can be classified from three perspectives: pathogenesis, red blood cell morphology, and clinical presentation. Pathogenic classification refers to the production or the inadequate production of erythrocytes and can be subdivided into two types, hypo-regenerative and regenerative. Hypo-regenerative anemia refers to a pathogenic condition in which the bone marrow production is decreased as a result of impaired function, decreased number of precursor cells, reduced bone marrow infiltration, or a lack of nutrients. Regenerative anemia refers to a pathogenic condition in which bone marrow response appropriately to a low erythrocyte mass by increasing the production of erythrocytes.

Anemia classified based on red blood cell morphology can be further subdivided into microcytic anemia, normocytic anemia, and macrocytic anemia. Microcytic anemia can be defined as the presence of small, hypochromic red blood cells in a peripheral blood smear and can also be characterized by a low mean corpuscular volume (MCV). Normocytic anemia can be defined as an anemia with a normal MCV range but with decreased hematocrit and/or hemoglobin values. Macrocytic anemia can be defined as the presence of larger than normal red blood cells.

Anemia is not necessarily a disease but is instead often a manifestation of an underlying disorder. The etiology behind anemia can be complex and to some degree, difficult to determine. For example, diagnosis of anemia can begin with a general physical checkup and a complete blood count (CBC) work-up. Based on the parameters from the CBC work-up, one or more additional tests are further carried out, sometimes requiring one or more additional hospital or clinical visits by the individual and/or long wait time between each test result.

In an illness or injury setting (e.g., a critical illness or injury setting), anemia can be common, and timing and accuracy are important factors for diagnosing the correct underlying cause of anemia. For example, anemia during a critical illness or injury can be resulted from either a shortened RBC circulatory life span or diminished RBC production. Causes of shortened life span can include hemolysis, phlebotomy losses, or bleeding due to either an injury site (e.g., a gastrointestinal bleeding) or an invasive procedure. Causes for diminished RBC production can be due to nutritional deficiencies or anemia of inflammation. In some instances, the anemia of inflammation may be a microcytic or hypochromic anemia, and the blood parameters of microcytic or hypochromic anemia can be similar or indistinguishable from those for iron deficiency anemia, thereby rendering the correct diagnosis complex and time-consuming.

Conventional methods of determining the underlying cause of anemia generally required multiple doctor's office visits (often to a specialist like a hematologist), multiple blood draws, and weeks or months of follow-up. Most primary care physicians are ill-equipped to order the necessary testing and follow-up required to make a determination and this commonly results in not only a lengthy delay in diagnosis, but also subjecting the patient to redundant or unnecessary tests. The conventional approach is resource and labor intensive and anemic patients are forced to wait for weeks or months before the underlying cause of the condition is determined.

Disclosed herein are processes and systems that automate and streamlines the diagnosis of anemia and an underlying cause behind the clinical presentation. In some instances, the processes and systems require only a single sample from an individual, thereby reducing and/or eliminating the need for returned visit(s) to a hospital or clinic by the individual. In some instances, the processes and systems are completed within 72 hours or less. In some cases, the processes are simplified to the essential tests required for diagnosis of each underlying cause of anemia, and optionally further reduce and/or eliminate complicated, time consuming, and potentially expensive diagnostic tests.

Method of Diagnosis

Disclosed herein, in certain embodiments, is an automated process for determining the presence and underlying cause of anemia in an individual in need thereof. In some embodiments, the automated process comprises obtaining a blood sample from an individual. Next, hemoglobin level and one or more red blood cell indices can be determined. Based on the hemoglobin level and values from the one or more red blood cell indices, one or more additional tests from a test panel can be carried out. A report based on the additional tests can be prepared and optionally forwarded to a physician, a third party for analysis, and/or the individual from which the blood sample is obtained. See FIG. 1A.

In some embodiments, the automated process is as illustrated in FIG. 1B. As illustrated herein, a first step comprises providing parameters on hemoglobin (Hb or Hgb) concentration and one or more red blood cell indices. Normal Hb concentration ranges may vary with the laboratory that performs the analysis. In some instances, a normal Hb concentration range for men is from about 13 mg/L (or about 13 g per deciliter (dL) or about 130 g per L) to about 17.5 mg/L (or about 17.5 g/dL or about 175 g/L), from about 13.1 mg/L (or about 13.1 g/dL or about 131 g/L) to about 17.5 mg/L (or about 17.5 g/dL or about 175 g/L), from about 13.1 mg/L (or about 13.1 g/dL or about 131 g/L) to about 16.6 mg/L (or about 16.6 g/dL or about 166 g/L), from about 13.2 mg/L (or about 13.2 g/dL or about 132 g/L) to about 17.5 mg/L (or about 17.5 g/dL or about 175 g/L), or from about 13.2 mg/L (or about 13.2 g/dL or about 132 g/L) to about 16.6 mg/L (or about 16.6 g/dL or about 166 g/L). In some cases, an abnormal Hb concentration for men is less than about 13 mg/L (or 13 g/dL or 130 g/L), less than about 13.1 mg/L (or 13.1 g/dL or 131 g/L), or less than about 13.2 mg/L (or 13.2 g/dL or 132 g/L). In some cases, the abnormal Hb concentration is indicative of anemia. In some cases, the normal range is also referred to herein as the defined standard for Hb concentration.

In some instances, a normal Hb concentration range for women is from about 11 mg/L (or about 11 g/dL or about 110 g/L) to about 15.3 mg/L (or about 15.3 g/dL or about 153 g/L), from about 11.6 mg/L (or about 11.6 g/dL or about 116 g/L) to about 15 mg/L (or about 15 g/dL or about 150 g/L), from about 11.7 mg/L (or about 11.7 g/dL or about 117 g/L) to about 15 mg/L (or about 15 g/dL or about 150 g/L), or from about 12 mg/L (or about 12 g/dL or about 120 g/L) to about 15 mg/L (or about 15 g/dL or about 150 g/L). In some cases, an abnormal Hb concentration for women is less than about 11 mg/L (or less than about 11 g/dL or less than about 110 g/L), less than about 11.6 mg/L (or 11.6 g/dL or 116 g/L), less than about 11.7 mg/L (or 11.7 g/dL or 117 g/L), or less than about 12 mg/L (or 12 g/dL or 120 g/L). In some cases, the abnormal Hb concentration is indicative of anemia. In some cases, the normal and abnormal Hb concentration ranges for women encompass a pregnant woman and/or a woman who is menstruating.

In some instances, an abnormal Hb concentration for a child less than 5 years of age is less than about 11 mg/L (or less than about 11 g/dL or less than about 110 g/L). In some cases, the abnormal Hb concentration is indicative of anemia.

In some cases, an abnormal Hb concentration for a child from about 5 years of age to about 12 years of age is less than about 11.5 mg/L (or less than about 11.5 g/dL or less than about 115 g/L). In some cases, the abnormal Hb concentration is indicative of anemia.

Red blood cell indices comprise measurements of mean cell volume (or mean corpuscular volume or MCV), mean cell hemoglobin (or mean corpuscular hemoglobin or MCH), and mean cell hemoglobin concentration (or mean corpuscular hemoglobin concentration or MCHC). MCV refers to the average size of the RBCs. Normal MCV values may vary with the laboratory that performs the analysis. In some instances, a normal range for MCV is from about 80 femtoliter (fL) to about 100 fL, from about 80 fL to about 98 fL, or from about 80 fL to about 96 fL. In some cases, a normal MCV value is associated with normocytic anemia (or normocytic normochromic anemia). In some cases, the normal range encompasses ranges for both men and women. In some cases, the normal range for MCV is also referred to herein as the defined standard for MCV.

In some cases, a high or elevated MCV is greater than about 96 fL, greater than about 97 fL, greater than about 98 fL, greater than about 99 fL, or greater than about 100 fL. In some cases, the high or elevated MCV is no higher than about 150 fL. In some cases, a high or elevated MCV value is associated with macrocytic anemia. In some cases, the high or elevated MCV value encompasses values for both men and women.

In some cases, a low MCV is less than about 80 fL or less than about 79 fL. In some cases, a low MCV is less than about 80 fL or less than about 79 fL but higher than about 50 fL. In some cases, the low MCV value is associated with microcytic anemia. In some cases, the low MCV value encompasses values for both men and women.

In some cases, a high MCV for a child is greater than about 86 fL, greater than about 87 fL, greater than about 95 fL, greater than about 98 fL, or greater than about 102 fL. In some cases, the child is less than or about 18 years of age. In some cases, a high MCV for a child less than about 2 years of age is greater than about 86 fL. In some cases, a high MCV for a child from about 2 years of age to about 6 years of age is greater than about 87 fL. In some cases, a high MCV for a child from about 6 years of age to about 12 years of age is greater than about 95 fL. In some cases, a high MCV for a child from about 12 years of age to about 18 years of age is greater than about 98 fL or greater than about 102 fL.

In some instances, a low MCV for a child is less than about 78 fL, less than about 77 fL, less than about 75 fL, or less than about 70 fL. In some cases, the child is less than or about 18 years of age. In some cases, a low MCV for a child less than about 2 years of age is less than about 70 fL. In some cases, a low MCV for a child from about 2 years of age to about 6 years of age is less than 75 fL. In some cases, a low MCV for a child from about 6 years of age to about 12 years of age is less than 77 fL. In some cases, a low MCV for a child from about 12 years of age to about 18 years of age is less than 78 fL.

MCH refers to the average quantity or amount of hemoglobin per red blood cell. Normal MCH values may vary with the laboratory that performs the analysis. In some instances, a normal range for MCH is from about 26 picograms (pg) to about 34 pg, from about 27 pg to about 34 pg, from about 27.5 pg to about 33.2 pg, from about 27 pg to about 33 pg, or from about 27 pg to about 31 pg. In some cases, a high MCH is greater than about 31 pg, greater than about 33 pg, greater about 33.2 pg, or greater than about 34 pg. In some cases, a low MCH is less than about 27.5 pg or less than about 27 pg. In some cases, the MCH values encompass ranges for both men and women. In some cases, the normal range for MCH is also referred to herein as the defined standard for MCH.

In some instances, a high MCH for a child is greater than about 30 pg, greater than about 31 pg, greater than about 33 pg, greater than about 34 pg, or greater than about 35 pg. In some cases, the child is less than or about 18 years of age. In some cases, a high MCH for a child less than about 2 years of age is greater than about 31 pg. In some cases, a high MCH for a child from about 2 years of age to about 6 years of age is greater than about 30 pg. In some cases, a high MCH for a child from about 6 years of age to about 12 years of age is greater than about 33 pg. In some cases, a high MCH for a child from about 12 years of age to about 18 years of age is greater than about 35 pg.

In some instances, a low MCH for a child is less than about 26 pg, less than about 25 pg, less than about 24 pg, or less than about 23 pg. In some cases, the child is less than or about 18 years of age. In some cases, a low MCH for a child less than about 2 years of age is less than about 23 pg. In some cases, a low MCH for a child from about 2 years of age to about 6 years of age is less than about 24 pg. In some cases, a low MCH for a child from about 6 years of age to about 18 years of age is less than 25 pg.

MCHC refers to the concentration of hemoglobin in a given volume of RBCs and can be calculated by dividing Hb by hematocrite (Hct). Normal MCHC values may vary with the laboratory that performs the analysis. In some instances, a normal range for MCHC is expressed as a mass and is from about 32 g/dL to about 36 g/dL, from about 33 g/dL to about 36 g/dL, or from about 33.4 g/dL to about 35.5 g/dL. In some cases, the normal range for MCHC is expressed as a molar concentration and is from about 4.81 mmol/L to about 5.58 mmol/L. In some cases, the normal range for MCHC is also expressed as a percentage (e.g., mass fraction of $m_{Hb}/m_{RBC}$) and is from about 32% to about 36%, from about 33% to about 36%, from about 33% to about 35%, or from about 32% to about 35%. In some cases, a high MCHC is greater than about 35 g/dL, greater than about 35.5 g/dL, or greater than about 36 g/dL. In some cases, a high MCHC is greater than about 5.58 mmol/L. In some cases, a high MCHC is greater than about 35% or greater than about 36%. In some cases, a low MCHC is less than about 33.4 g/dL, less than about 33 g/dL, or less than about 32 g/dL. In some cases, a low MCHC is less than about 4.81 mmol/L. In some cases, a low MCHC is less than about 33% or less than about 32%. In some cases, the MCHC values encompass ranges for both men and women. In some cases, the normal range for MCHC values is also referred to herein as the defined standard for MCHC.

In some instances, a high MCHC for a child is greater than about 36%. In some cases, the child is less than or about 18 years of age.

In some cases, a low MCHC for a child is less than about 32% or 30%. In some cases, the child is less than or about 18 years of age. In some cases, a low MCHC for a child less than 2 years of age is less than about 30%. In some cases, a low MCHC for a child from about 2 years of age to about 18 years of age is less than about 32%.

In some embodiments, the first step of the disclosed methods comprises measuring Hb concentration in combination with MCV, MCH, and/or MCHC. In some instances, the first step comprises measuring Hb concentration, MCV, and MCHC. In some instances, the first step is a complete blood count (CBC), which provides measurements of Hb concentration, MCV, and MCHC.

In some instances, the CBC provides additional parameters such as hematocrite, white blood cell (WBC) count, platelet count, platelet distribution width (PDW), mean platelet volume (MPV), red blood cell count, red cell distribution width (RDW), and cell morphology. Hematocrit (Hct) determines the percentage of RBCs in the blood. In some instances, a normal range for men is from about 38% to about 51%, from about 38.3% to about 48.6%, or from about 41.5% to about 50.4%. In some cases, a range that is less than about 41.5%, less than about 41%, less than about 39%, less than about 38.3%, or less than about 38% is indicative of anemia.

In some cases, a normal range of Hct for women is from about 35% to about 45%, from about 35.5% to about 44.9%, or from about 36.9% to about 44.6%. In some cases, a range that is less than about 36.9%, less than about 36%, less than about 35.5%, or less than about 35% is indicative of anemia.

A WBC count measures the number of white blood cells in the blood. In some cases, a normal range for a white blood cell count is from about 3.4 to about 9.6 billion cells/L (or from about 3400 to about 9600 cells/mcL). A WBC count can also be measured as a cell differential, which determines the percentage of each type of white blood cells present in the blood, or as nuclear segmentation of neutrophils.

A platelet count measures the number of platelets in the blood. In some instances, a normal range is from about 150,000 to about 450,000 platelets/mcL. In some cases, a normal range for men is from about 135 to about 317 billion/L (or from about 135,000 to about 317,000 platelets/mcL). In some cases, a normal range for women is from about 157 to about 371 billion/L (or from about 157,000 to about 371,000 platelets/mcL).

A platelet distribution width (PDW) measures the variation of platelet size and a normal range is from about 8.3 to about 25 fL.

A mean platelet volume (MPV) refers to the average size of the platelets in the blood and a normal range is from about 8.6 to about 15.5 fL.

A red blood cell count measures the number of RBCs in the blood. In some instances, a normal range for men is from about 4.35 to about 5.65 trillion cells/L (or from about 4.32 to about 5.72 million cells/mcL). In some cases, a normal range for women is from about 3.92 to about 5.13 trillion cells/L (or from about 3.9 to about 5.03 million cells/mcL).

A red cell distribution width refers to the variation of RBC size. In some instances, a normal range for men is from about 11.8% to about 14.5% and a normal range for women is from about 12.2% to about 16.1%.

In some cases, cell morphology comprises anisocytosis, poikilocytosis, and polychromasia. Anisocytosis refers to a condition in which the RBCs are unequal in size. Poikilocytosis refers to the presence of a variation in cell shape, e.g., as oval, teardrop-shaped, sickle-shaped, or irregularly contracted RBCs. Polychromasia refers to a condition in which an abnormally high number of immature RBCs are present in the blood.

In some embodiments, based on the values of MCHC, Hb concentration, and MCV, one or more additional panel of tests (or cascades) are carried out in a subsequent step. In some instances, if the value of MCHC is high or increased above a normal range, a reticulocyte count is carried out. Reticulocyte count measures the number of newly produced, relatively immature RBCs in the blood. The newly produced RBCs contain residual nuclear material termed reticulins and the presence of the immature RBCs can be a reflection of recent bone marrow function and/or activity. In some instances, the reticulocyte count is reflected as a reticulocyte percentage. In some cases, a normal range of the reticulocyte count is from about 0.5% to about 2.5%, from about 0.5% to about 2%, or from about 0.5% to about 1.5%. In some cases, an elevated reticulocyte count is greater than 1.5%, greater than 2%, or greater than 2.5%. In some instances, the reticulocyte count is measured as an absolute reticulocyte count. In some cases, a normal range of the reticulocyte count is from about $10\times10^9$ to about $110\times10^9$ RBCs/L, from about $50\times10^9$ to about $100\times10^9$ RBCs/L, or from about $50\times10^9$ to about $150\times10^9$ RBCs/L. In some cases, an elevated reticulocyte count is greater than $100\times10^9$ RBCs/L, greater than $110\times10^9$ RBCs/L, or greater than $150\times10^9$ RBCs/L. In some instances, the reticulocyte count is encompassed within a CBC. In other instances, the reticulocyte count is a separate test. In some cases, a test panel comprising reticulocyte count is referred to herein as Cascade 1 (also see Table 1 and FIG. 1B).

In some instances, if the value of MCHC falls within the normal range or is below the normal range, the Hb concentration falls below the normal range, and the MCV value falls below the normal range, a panel of test comprising a reticulocyte count and ferritin and optionally a hemoglobinopathy evaluation is carried out. A ferritin test measures the amount of ferritin in the blood. In some instances, a normal range of ferritin (or serum ferritin) for men is from about 12 to about 300 ng/mL, from about 20 to about 300 ng/mL, or from about 20 to about 250 ng/mL. In some cases, an elevated level of ferritin for men is greater than about 250 ng/mL or greater than about 300 ng/mL. In some instances, a normal range of ferritin (or serum ferritin) for women is from about 12 to about 270 ng/mL, from about 12 to about 263 ng/mL, from about 20 to about 200 ng/mL, from about 12 to about 150 ng/mL, or from about 10 to about 120 ng/mL. In some cases, an elevated level of ferritin for women is greater than about 120 ng/mL, greater than about 150 ng/mL, greater than about 200 ng/mL, greater than about 263 ng/mL, or greater than about 270 ng/mL. In some cases, a decreased or low level of ferritin is less than about 20 ng/mL, less than about 12 ng/mL, or less than 10 ng/mL.

In some cases, a normal range of ferritin (or serum ferritin) in a child is from about 7 to about 140 ng/mL. In some cases, the child is less than about 18 years of age, or less than about 15 years of age.

Hemoglobinopathy evaluation is a group of tests that detects and identifies the type of hemoglobinopathy. Hemoglobinopathy is an inherited blood disorder and is characterized by an abnormal form of hemoglobin (or variant) or by a decreased production of hemoglobin (e.g., thalassemia). In some instances, a hemoglobinopathy evaluation detects the presence of a hemoglobin variant such as hemoglobin A, hemoglobin A2, hemoglobin F, hemoglobin S, hemoglobin C, and hemoglobin E. In some cases, the hemoglobinopathy evaluation detects β-thalassemia. In some cases, the hemoglobinopathy evaluation does not detect α-thalassemia. In some cases, a separate genetic testing is carried out to detect the presence of α-thalassemia.

In some instances, the panel of test comprising a reticulocyte count, ferritin, and hemoglobinopathy evaluation is referred to herein as Cascade 2 (also see Table 1 and FIG. 1B).

In some instances, if the value of MCHC falls within the normal range or is below the normal range, the Hb concentration falls below the normal range, and the MCV value is within the normal range, a panel of test comprising reticulocyte count, ferritin, and optionally C-reactive protein (CRP) and/or comprehensive metabolic panel (CMP) is carried out. C-reactive protein (CRP) is a liver protein and the CRP level increases in the presence of an inflammation. A CRP test measures the level of CRP in the blood. In some instances, a normal range of CRP is from about 0.2 mg/L to about 6.1 mg/L, from about 0.2 mg/L to about 6 mg/L, or from about 0.2 mg/L to about 5 mg/L. In some cases, a high or elevated CRP level is greater than about 5 mg/L, greater than about 6 mg/L, or greater than about 6.2 mg/L.

Comprehensive metabolic panel (CMP) is a test that measures about 14 different parameters in the blood and includes glucose, calcium, sodium, potassium, carbon dioxide, chloride, albumin, total protein, alkaline phosphatase (ALP), alanine transaminase (ALT), aspartate aminotransferase (AST), bilirubin, blood urea nitrogen (BUN), and creatinine. In some instances, a normal range for glucose is from about 65 mg/dL to about 100 mg/dL. In some cases, a normal range for BUN is from about 5 to about 26 mg/dL. In some cases, a normal range for creatinine is from about 0.76 mg/dL to about 1.27 mg/dL. In some cases, a normal range for sodium is from about 135 mmol/L to about 145 mmol/L. In some cases, a normal range for potassium is from about 3.5 mmol/L to about 5.2 mmol/L. In some cases, a normal range for chloride is from about 97 mmol/L to about 108 mmol/L. In some cases, a normal range for carbon dioxide is from about 20 mmol/L to about 32 mmol/L. In some cases, a normal range for calcium is from about 8.5 mg/dL to about 10.6 mg/dL. In some cases, a normal range for albumin is from about 3.6 g/dL to about 4.8 g/dL or from about 3.5 g/dL to about 5 g/dL. In some cases, a normal range for total protein is from about 6 g/dL to about 8.5 g/dL or from about 6.3 g/dL to about 7.9 g/dL. In some cases, a normal range for bilirubin (e.g., total bilirubin) is from about 0.1 mg/dL to about 1.2 mg/dL. In some cases, a normal range for ALP is from about 25 IU/L to about 160 IU/L or from about 40 IU/L to about 129 IU/L. In some cases, a normal range for AST is from about 0 IU/L to about 40 IU/L or from about 8 IU/L to about 48 IU/L. In some cases, a normal range for ALT is from about 0 IU/L to about 55 IU/L or from about 7 IU/L to about 55 IU/L.

In some cases, the panel of test comprising a reticulocyte count, ferritin, C-reactive protein, and comprehensive metabolic panel is referred to herein as Cascade 3 (also see Table 1 and FIG. 1B).

In some instances, if the MCV value is elevated and the Hb concentration falls below the normal range, a panel of test comprising reticulocyte count, folate test, vitamin B12, and optionally hepatic function panel is carried out. A folate test (or a folic acid test) measures the amount of folic acid in the blood. As used herein, the term "folate" encompasses folic acid or a derivatives thereof, a reduced form of folate, and 5-methyltetrahydrofolic acid. Folic acid or N-[4-(2-Amino-3,4-dihydro-4-oxo-6-pteridinylmethylamino)-benzoyl]-L-glutamic acid), is also known as vitamin B9, folicin, N-pteroyl-L-glutamic acid, and N-pteroyl-L-glutamate. Exemplary reduced forms of folate include, but are not limited to, 6(R,S)-5-methyltetrahydrofolate (6(S)-5-methyltetrahydrofolate, 10-methylenetetrahydrofolate, 10-formyltetrahydrofolic acid, 5-formyltetrahydrofolic acid, 5-forminino tetrahydrofolic acid, 5,10-methenyltetrahydrofolic acid, 5,10-methyltetrahydrofolic acid, L-methylfolate, 6(R,S)-5-formyltetrahydrofolate (folinic acid), and tetrahydrofolic acid/tetrahydrofolate.

In some instances, a folate test is conducted on the blood plasma. In such instances, a normal range is from about 2 ng/mL to about 10 ng/mL or from about 2.7 ng/mL to about 17 ng/mL. In some instances, a folate test is conducted on RBCs. In such instances, a normal range is from about 140 ng/mL to about 960 ng/mL. In some cases, a reduced or low folate level is less than about 2.7 ng/mL or less than about 2 ng/mL if the test is conducted on blood plasma. In additional cases, a reduced or low folate level is less than about 140 ng/mL if the test is conducted on RBCs.

A vitamin B12 test measures the amount of vitamin B12 in the blood. Vitamin B12, also called cobalamin, is a water soluble vitamin and as used herein refers to a group of cobalt-containing vitamin compounds known as cobalamins: they include cyanocobalamin, hydroxocobalamin, and two naturally occurring cofactor forms of $B_{12}$ the human body: 5'-deoxyadenosylcobalamin (adenosylcobalamin—AdoB12), the cofactor of Methylmalonyl Coenzyme A mutase (MUT), and methylcobalamin ($MeB_{12}$), the cofactor of 5-methyltetrahydrofolate-homocysteine methyltransferase (MTR). In some instances, a normal vitamin B12 range is from about 200 to about 900 ng/mL. In some cases, a reduced or low vitamin B12 level is less than about 200 ng/mL.

A hepatic function panel measures the level of total protein, albumin, bilirubin, and liver enzymes such as alkaline phosphatase (ALP), alanine transaminase (ALT), and aspartate aminotransferase (AST) in the blood. In some cases, a normal range for total protein is from about 6 g/dL to about 8.5 g/dL or from about 6.3 g/dL to about 7.9 g/dL. In some cases, a normal range for albumin is from about 3.6 g/dL to about 4.8 g/dL or from about 3.5 g/dL to about 5 g/dL. In some cases, a normal range for bilirubin (e.g., total bilirubin) is from about 0.1 mg/dL to about 1.2 mg/dL. In some cases, a normal range for ALP is from about 25 IU/L to about 160 IU/L or from about 40 IU/L to about 129 IU/L.

In some cases, a normal range for ALT is from about 0 IU/L to about 55 IU/L or from about 7 IU/L to about 55 IU/L. In some cases, a normal range for AST is from about 0 IU/L to about 40 IU/L or from about 8 IU/L to about 48 IU/L.

In some cases, the panel of test comprising a reticulocyte count, folate test, vitamin B12, and hepatic function panel is referred to herein as Cascade 4 (also see Table 1 and FIG. 1B).

In some embodiments, disclosed herein is an automated process for determining the cause of anemia comprising;

(a) assessing in a blood sample from an individual with anemia mean corpuscular hemoglobin concentration (MCHC) of the sample and comparing the MCHC level in the sample to a defined standard for MCHC;

(b-i) if the MCHC level in the sample in (a) is elevated compared to the defined standard for MCHC, assessing reticulocyte count of the sample and comparing the reticulocyte count of the sample to a defined standard reticulocyte count;

(c) if the reticulocyte count of the sample in (b-i) is normal or elevated compared to the defined standard reticulocyte count, recommending genetic testing of a hemolytic anemia condition;

(b-ii) if the MCHC level in the sample in (a) is not elevated compared to the defined standard for MCHC or if the reticulocyte count of the sample in (b-i) is low compared to the defined standard reticulocyte count, assessing hemoglobin level in the sample and comparing the hemoglobin level in the sample to a defined cutoff for hemoglobin;

(d-i) if the hemoglobin level in the sample in (b-ii) is not lower than the defined cutoff for hemoglobin, recommending no further testing;

(d-ii) if the hemoglobin level in the sample in (b-ii) is lower than the defined cutoff for hemoglobin, assessing reticulocyte count of the sample and comparing the reticulocyte count of the sample to a defined standard reticulocyte count, and assessing mean corpuscular volume (MCV) and comparing the MCV of the sample to a defined standard for MCV;

(e-i) if the MCV in the sample in (d-ii) is low compared to the defined standard for MCV, assessing ferritin level in the sample and comparing the ferritin level to a defined cutoff for ferritin;

(f-i) if the ferritin level in (e-i) is low compared to the defined cutoff for ferritin, suggesting the individual is iron deficient or recommending further testing of an alpha thalassemia hemoglobinopathy;

(f-ii) if the ferritin level in (e-i) is normal or high compared to the defined cutoff for ferritin, assessing reticulocyte count of the sample and comparing the reticulocyte count of the sample to a defined standard reticulocyte count and performing a hemoglobinopathy evaluation;

(g-i) if the reticulocyte count in (f-ii) is not elevated and the hemoglobinopathy evaluation is normal, suggesting the individual has anemia of a chronic disease;

(g-ii) if the reticulocyte count in (f-ii) is elevated and the hemoglobinopathy evaluation is normal, suggesting the individual has a hemolytic anemia; and (g-iii) if the reticulocyte count in (f-ii) is normal or elevated and the hemoglobinopathy evaluation is abnormal, suggesting the individual has anemia of a hemoglobinopathy;

(e-ii) if the MCV in the sample in (d-ii) is elevated by at least 10% compared to the defined standard for MCV, assessing B12 and/or folate levels in the sample and comparing the B12 and/or folate levels to a defined cutoffs for B12 and/or folate;

(h-i) if the B12 and/or folate levels in the sample in (e-ii) are lower than the defined cutoffs for B12 and/or folate, assessing methylmalonic acid content of the sample to confirm or exclude a B12 and/or folate deficiency;

(h-ii) if the B12 and/or folate levels in the sample in (e-ii) are higher than the defined cutoffs for B12 and/or folate, assessing reticulocyte count of the sample and comparing the reticulocyte count of the sample to a defined standard reticulocyte count;

(i-i) if the reticulocyte count of the sample in (h-ii) is normal or elevated compared to the defined standard reticulocyte count, recommending genetic testing of a hemolytic anemia condition;

(i-ii) if the reticulocyte count of the sample in (h-ii) is low compared to the defined standard reticulocyte count, assessing one or more markers of liver function in the sample and comparing the one or more markers of liver function in the sample to a defined range for the one or more markers of liver function;

(j-i) if the one or more markers of liver function in (i-ii) are within the defined range for the one or more markers of liver function, suggesting that the individual is assessed for a hematological disease; and (j-ii) if the one or more markers of liver function in (i-ii) are within the defined range for the one or more markers of liver function, suggesting that the individual is assessed for chronic disease secondary to liver disease with or without alcohol.

(e-iii) if the MCV in the sample in (d-ii) is normal compared to the defined standard for MCV, assessing ferritin level in the sample and comparing the ferritin level to a defined cutoff for ferritin;

(k-i) if the ferritin level in (e-iii) is low compared to the defined cutoff for ferritin, suggesting the individual is iron deficient (which may be caused by an acute or chronic phase reaction) and recommending further evaluation of iron deficiency;

(k-ii) if the ferritin level in (e-iii) is high compared to the defined cutoff for ferritin, suggesting the individual is having an acute or chronic phase reaction and recommending further clinical evaluation;

(k-iii) if the ferritin level in (e-iii) is normal compared to the defined cutoff for ferritin, assessing reticulocyte count of the sample and comparing the reticulocyte count of the sample to a defined standard reticulocyte count, and assessing C-reactive protein (CRP) level in the sample and comparing the CRP level in the sample to a defined cutoff for CRP;

(l-i) if the reticulocyte count and CRP in (k-iii) are normal, recommending further evaluation for chronic disease or dimorphic anemia;

(l-ii) if the reticulocyte count in (k-iii) is increased and CRP in (l-iii) is normal, recommending further evaluation for hemolytic anemia or gastrointestinal bleeding;

(l-iii) if the reticulocyte count in (k-iii) is low or normal and the CRP in (l-iii) is increased, performing a complete metabolic panel (CMP), and if the CMP is abnormal, suggesting the individual has anemia of chronic disease.

In some embodiments, the hemolytic anemia condition for which genetic testing is recommended is hereditary xerocytosis (HX), sickle cell anemia, and/or hereditary spherocytosis. In some embodiments, the defined cutoff for hemoglobin is about 13.2 mg/l for an adult male and about 11.7 mg/l for an adult female. In some embodiments, the hemoglobinopathy evaluation comprises assessing hemoglobin A, hemoglobin F, total hemoglobin, hemoglobin A2 (Quant), hemoglobin S, hemoglobin C, hemoglobin E and any hemoglobin variants. In some embodiments, the hemoglobinopathy evaluation further comprises a red blood cell count, a hematocrit, assessing mean corpuscular volume (MCV), assessing mean corpuscular hemoglobin (MCH), and red blood cell distribution width (RDW). In some embodiments, the hematological disease is myelodysplasia or a hematological malignancy. In some embodiments, only a single blood sample is obtained from the individual. In some embodiments, the process is completed in 72 hours or less. In some embodiments, the individual is not under treatment for iron deficiency. In some embodiments, the individual does not have a family history of red blood cell disorders. In some embodiments, the blood sample was obtained by or under the direction of a primary care physician.

In some embodiments, also disclosed herein is an automated process to determine the underlying cause of microcytic anemia comprising:

(a) determining the amount of ferritin in a blood sample from an individual with anemia and a mean corpuscular volume (MCV) is lower than a defined cutoff of about 80 fL or about 79 fL;

(i) if the ferritin level in is low compared to the defined cutoff for ferritin, suggesting the individual is iron deficient or recommending further testing of an alpha thalassemia hemoglobinopathy;

(ii) if the ferritin level in is normal or high compared to the defined cutoff for ferritin, assessing reticulocyte count of the sample and comparing the reticulocyte count of the sample to a defined standard reticulocyte count and performing a hemoglobinopathy evaluation;

(A) if the reticulocyte count in (ii) is not elevated and the hemoglobinopathy evaluation is normal, suggesting the individual has anemia of a chronic disease;

(B) if the reticulocyte count in (ii) is elevated and the hemoglobinopathy evaluation is normal, suggesting the individual has a hemolytic anemia; and (C) if the reticulocyte count in (ii) is normal or elevated and the hemoglobinopathy evaluation is abnormal, suggesting the individual has anemia of a hemoglobinopathy.

In some embodiments, the individual has low hemoglobin and a normal mean corpuscular hemoglobin concentration (MCHC). In some embodiments, the hemoglobinopathy evaluation comprises assessing hemoglobin A, hemoglobin F, total hemoglobin, hemoglobin A2 (Quant), hemoglobin S, hemoglobin C, hemoglobin E and any hemoglobin variants. In some embodiments, the hemoglobinopathy evaluation further comprises a red blood cell count, a hematocrit, assessing mean corpuscular volume (MCV), assessing mean corpuscular hemoglobin (MCH), and red blood cell distribution width (RDW). In some embodiments, only a single blood sample is obtained from the individual. In some embodiments, the process is completed in 72 hours or less.

In some embodiments, further disclosed herein is an automated process to determine the underlying cause of normocytic anemia comprising:

(a) determining the amount of ferritin in a blood sample from an individual with anemia and a mean corpuscular volume (MCV) is within the range of from about 80 fL to about 100 fL, from about 80 fL to about 98 fL, or from about 80 fL to about 96 fL;

(i) if the ferritin level is low compared to the defined cutoff for ferritin, suggesting the individual is iron deficient and recommending further evaluation of iron deficiency;

(ii) if the ferritin level is high compared to the defined cutoff for ferritin, suggesting the individual is having an acute or chronic phase reaction and recommending further clinical evaluation;

(iii) if the ferritin level is normal compared to the defined cutoff for ferritin, assessing reticulocyte count of the sample and comparing the reticulocyte count of the sample to a defined standard reticulocyte count, and assessing C-reactive protein (CRP) level in the sample and comparing the CRP level in the sample to a defined cutoff for CRP;

(A) if the reticulocyte count and CRP in (iii) are normal, recommending further evaluation for chronic disease or dimorphic anemia;

(B) if the reticulocyte count in (iii) is increased and CRP in (l-iii) is normal, recommending further evaluation for hemolytic anemia or gastrointestinal bleeding;

(C) if the reticulocyte count in (iii) is low or normal and the CRP in (l-iii) is increased, performing a complete metabolic panel (CMP), and if the CMP is abnormal, suggesting the individual has anemia of chronic disease.

In some embodiments, the individual has low hemoglobin and a normal mean corpuscular hemoglobin concentration (MCHC). In some embodiments, only a single blood sample is obtained from the individual. In some embodiments, the process is completed in 72 hours or less In some embodiments, additionally disclosed herein is an automated process to determine the underlying cause of macrocytic anemia comprising:

(a) determining the amount of B12 and/or folate in a blood sample from an individual with anemia and a mean corpuscular volume (MCV) is at least 10% more than a defined cutoff of about 96 fL, about 97 fL, about 98 fL, about 99 fL, or about 100 fL;

(i) if the B12 and/or folate levels in the sample in are lower than defined cutoffs for B12 and/or folate, assessing methylmalonic acid content of the sample to confirm or exclude a B12 and/or folate deficiency;

(ii) if the B12 and/or folate levels in the sample in are higher than the defined cutoffs for B12 and/or folate, assessing reticulocyte count of the sample and comparing the reticulocyte count of the sample to a defined standard reticulocyte count;

(A) if the reticulocyte count of the sample in (ii) is normal or elevated compared to the defined standard reticulocyte count, recommending genetic testing of a hemolytic anemia condition;

(B) if the reticulocyte count of the sample in (ii) is low compared to the defined standard reticulocyte count, assessing one or more markers of liver function in the sample and comparing the one or more markers of liver function in the sample to a defined range for the one or more markers of liver function;

(I) if the one or more markers of liver function in (B) are within the defined range for the one or more markers of liver function, suggesting that the individual is assessed for a hematological disease; and (II) if the one or more markers of liver function in (B) are within the defined range for the one or more markers of liver function, suggesting that the individual is assessed for chronic disease secondary to liver disease with or without alcohol.

In some embodiments, the individual has low hemoglobin and a normal mean corpuscular hemoglobin concentration (MCHC). In some embodiments, the hemolytic anemia condition for which genetic testing is recommended is hereditary xerocytosis (HX), sickle cell anemia, and/or hereditary spherocytosis. In some embodiments, only a single blood sample is obtained from the individual.

Further still, in some embodiments, disclosed herein is automated process for determining an underlying cause of anemia, comprising: determining from a blood sample obtained from an individual suspected of having anemia, by a processing module, a hemoglobin level, mean corpuscular hemoglobin concentration (MCHC), and mean corpuscular volume (MCV); comparing the hemoglobin level, MCHC level, and MCV value to a defined standard for hemoglobin level, MCHC, and MCV; and (i) assessing reticulocyte count, by the same processing module or by an additional processing module, if the MCHC level is elevated compared to the defined standard for MCHC; or (ii) assessing reticulocyte count, ferritin level, and hemoglobinopathy evaluation, by the same processing module and/or at least an additional processing module, if the hemoglobin level is lower than the defined standard for hemoglobin level, the MCV value is lower than the defined standard for MCV, and the MCHC level is normal or lower than the defined standard for MCHC; or (iii) assessing reticulocyte count, ferritin level, C-reactive protein (CRP), and comprehensive metabolic panel (CMP), by the same processing module and/or at least an additional processing module, if the hemoglobin level is lower than the defined standard for hemoglobin level, the MCV value is normal compared to the defined standard for MCV, and the MCHC level is normal or lower than the defined standard for MCHC; or (iv) assessing reticulocyte count, folate, vitamin B12, and hepatic function panel, by the same processing module and/or at least an additional processing module, if the hemoglobin level is lower than the defined standard for hemoglobin level, and the MCV value is elevated by at least about 10% compared to the defined standard for MCV.

In some embodiments, the process further comprises comparing the reticulocyte count of step i) with a defined standard, wherein an elevated reticulocyte count is indicative of hemolytic anemia or gastrointestinal bleeding.

In some embodiments, the process further comprises comparing the ferritin level of step ii) with a defined standard, wherein a reduced level of ferritin is indicative of iron deficiency.

In some embodiments, the process further comprises comparing the reticulocyte count, ferritin level, and hemoglobinopathy evaluation of step ii) with their respective defined standards, wherein: a) a normal or elevated level of ferritin, a normal hemoglobinopathy evaluation and a normal reticulocyte count are indicative of anemia of chronic disease; b) a normal or elevated level of ferritin, a normal hemoglobinopathy evaluation, and an elevated reticulocyte count are indicative of hemolytic anemia; or c) a normal or elevated level of ferritin, an abnormal hemoglobinopathy evaluation, and a normal or elevated reticulocyte count are indicative of anemia of a hemoglobinopathy.

In some embodiments, the process further comprises comparing the ferritin level of step iii) with a defined standard, wherein a reduced level of ferritin is indicative of iron deficiency, optionally early iron deficiency.

In some embodiments, the process further comprises comparing the ferritin level of step iii) with a defined standard, wherein an elevated level of ferritin is indicative of an acute phase reaction.

In some embodiments, the process further comprises comparing the ferritin level, CRP, CMP, and the reticulocyte count of step iii) with their respective defined standards, wherein: a) a normal level of ferritin and an elevated reticulocyte count are indicative of hemolytic anemia or gastrointestinal bleeding; b) a normal level of ferritin, a low or normal reticulocyte count, an elevated level of CRP, and an abnormal or normal CMP are indicative of anemia of chronic disease (ACD); or c) a normal level of ferritin, a normal reticulocyte count, and a normal level of CRP are indicative of chronic disease or dimorphic anemia.

In some embodiments, the process further comprises comparing folate and vitamin B12 of step iv) with their respective defined standards, wherein either a low level of folate or vitamin B12 is indicative of folate or vitamin B12 deficiency. In some instances, a methylmelonic acid test is further carried out to confirm a vitamin B12 deficiency.

In some embodiments, the process further comprises comparing the reticulocyte count, folate, and vitamin B12 of step iv) with their respective defined standards, wherein either a low level of folate or vitamin B12 and an elevated reticulocyte count are indicative of hemolytic anemia.

In some embodiments, the process further comprises comparing the reticulocyte count, folate, vitamin B12, and the hepatic function panel of step iv) with their respective defined standards, wherein: a) either a low level of folate or vitamin B12, an elevated reticulocyte count, and a normal hepatic function are indicative of a hematologic disease; or b) either a low level of folate or vitamin B12, an elevated reticulocyte count, and an abnormal hepatic function are indicative of anemia of chronic disease, optionally secondary to a liver disease, further optionally associated with alcohol.

In some embodiments, the hemolytic anemia comprises an inherited hemolytic anemia or an acquired hemolytic anemia.

In some embodiments, the inherited hemolytic anemia comprises sickle cell anemia, thalassemia, hereditary xerocytosis, hereditary spherocytosis, hereditary elliptocytosis (ovalocytosis), glucose-6-phosphate dehydrogenase (G6PD) deficiency, and pyruvate kinase deficiency.

Known causes of hemolytic anemia include, but are not limited to, inherited conditions, such as sickle cell anemia and thalassemia; stressors such as infections, drugs, snake or spider venom, or certain foods; toxins from advanced liver or kidney disease; inappropriate attack by the immune system; vascular grafts, prosthetic heart valves, tumors, severe burns, exposure to certain chemicals, severe hypertension, or clotting disorders; and in rare cases, an enlarged spleen. Accordingly, in some embodiments, the acquired hemolytic anemia comprises immune hemolytic anemia, mechanical hemolytic anemias, paroxysmal nocturnal hemoglobinuria, pathogen-induced acquired hemolytic anemia, and chemical-induced acquired hemolytic anemia.

In some embodiments, the immune hemolytic anemia comprises autoimmune hemolytic anemia (AIHA), alloimmune hemolytic anemia, and drug-induced hemolytic anemia.

In some embodiments, the pathogen-induced acquired hemolytic anemia comprises one or more pathogens that damage red blood cells, optionally comprising protozoans from the genus *Plasmodium* or bacteria from the genus *Borrelia*. In some instances, *Plasmodium* comprises *P. falciparum, P. malariae, P. ovale*, and *P. vivax*. In some instances, *Borrelia* comprises *B. burgdorferi, B. mayonii, B. afzelii*, and *B. garinii.*

In some embodiments, the chemical-induced acquired hemolytic anemia comprises one or more chemicals that damage red blood cells, optionally comprising toxic chemicals or venom.

In some embodiments, the hematologic disease comprises myelodysplasia.

In some instances, the hemoglobinopathy evaluation detects the presence of a hemoglobin variant and/or thalassemia.

In some instances, the hemoglobin variant comprises hemoglobin A, hemoglobin A2, hemoglobin F, hemoglobin S, hemoglobin C, or hemoglobin E.

In some instances, the hemoglobinopathy evaluation does not detect the presence of α-thalassemia.

In some instances, the process does not comprise a blood smear test.

In some instances, the process does not detect and/or assess red cell distribution width (RWD).

In some instances, the process comprises carrying out a complete blood count (CBC) test to detect the hemoglobin level, MCHC, and MCV.

In some instances, the process is completed in about 72 hours or less.

In some instances, the individual is not under a treatment for iron deficiency.

In some instances, a single blood sample is obtained from the individual.

In some instances, the comparing step is carried out by a processor.

In some embodiments, a process described herein provides an improved specificity for diagnosing the underlying cause of anemia. In some instances, the improved specificity is a 2-fold, 3-fold, 4-fold, 5-fold, 6-fold, 7-fold, 8-fold, 9-fold, 10-fold, 20-fold, 50-fold, or higher improvement compared to a standard method, e.g., a standard clinical method.

In some embodiments, a process described herein further provides an improved sensitivity for diagnosing the underlying cause of anemia. In some instances, the improved sensitivity is a 2-fold, 3-fold, 4-fold, 5-fold, 6-fold, 7-fold, 8-fold, 9-fold, 10-fold, 20-fold, 50-fold, or higher improvement compared to a standard method, e.g., a standard clinical method.

Systems and Samples for Determining the Presence and Underlying Cause of Anemia

Disclosed herein, in certain embodiments, is a system for automated processing of a blood sample to determine an underlying cause of anemia, comprising: a memory; a display; and at least one processor coupled to the memory programmed with executable instructions, the instructions comprise: (a) determining from a blood sample obtained from an individual suspected of having anemia a hemoglobin level, mean corpuscular hemoglobin concentration (MCHC), and mean corpuscular volume (MCV); (b) comparing the hemoglobin level, MCHC level, and MCV value to a defined standard for hemoglobin level, MCHC, and MCV; and (i) assessing reticulocyte count if the MCHC level is elevated compared to the defined standard for MCHC; or (ii) assessing reticulocyte count, ferritin level, and hemoglobinopathy evaluation if the hemoglobin level is lower than the defined standard for hemoglobin level, the MCV value is lower than the defined standard for MCV, and the MCHC level is normal or lower than the defined standard for MCHC; or (iii) assessing reticulocyte count, ferritin level, C-reactive protein (CRP), and comprehensive metabolic panel (CMP) if the hemoglobin level is lower than the defined standard for hemoglobin level, the MCV value is normal compared to the defined standard for MCV, and the MCHC level is normal or lower than the defined standard for MCHC; or (iv) assessing reticulocyte count, folate, vitamin B12, and hepatic function panel if the hemoglobin level is lower than the defined standard for hemoglobin level, and the MCV value is elevated by at least about 10% compared to the defined standard for MCV.

In some embodiments, the instructions further comprise comparing the reticulocyte count of step i) with a defined standard, wherein an elevated reticulocyte count is indicative of hemolytic anemia or gastrointestinal bleeding.

In some embodiments, the instructions further comprise comparing the ferritin level of step ii) with a defined standard, wherein a reduced level of ferritin is indicative of iron deficiency.

In some embodiments, the instructions further comprise comparing the reticulocyte count, ferritin level, and hemoglobinopathy evaluation of step ii) with their respective defined standards, wherein: a) a normal or elevated level of ferritin, a normal hemoglobinopathy evaluation and a normal reticulocyte count are indicative of anemia of chronic disease; b) a normal or elevated level of ferritin, a normal hemoglobinopathy evaluation, and an elevated reticulocyte count are indicative of hemolytic anemia; or c) a normal or elevated level of ferritin, an abnormal hemoglobinopathy evaluation, and a normal or elevated reticulocyte count are indicative of anemia of a hemoglobinopathy.

In some embodiments, the instructions further comprise comparing the ferritin level of step iii) with a defined standard, wherein a reduced level of ferritin is indicative of iron deficiency, optionally early iron deficiency.

In some embodiments, the instructions further comprise comparing the ferritin level of step iii) with a defined standard, wherein an elevated level of ferritin is indicative of an acute phase reaction.

In some embodiments, the instructions further comprise comparing the ferritin level, CRP, CMP, and the reticulocyte count of step iii) with their respective defined standards, wherein: a) a normal level of ferritin and an elevated reticulocyte count are indicative of hemolytic anemia or gastrointestinal bleeding; b) a normal level of ferritin, a low or normal reticulocyte count, an elevated level of CRP, and an abnormal or normal CMP are indicative of anemia of chronic disease (ACD); or c) a normal level of ferritin, a normal reticulocyte count, and a normal level of CRP are indicative of chronic disease or dimorphic anemia.

In some embodiments, the instructions further comprise comparing folate and vitamin B12 of step iv) with their respective defined standards, wherein either a low level of folate or vitamin B12 is indicative of folate or vitamin B12 deficiency.

In some embodiments, the instructions further comprise comparing the reticulocyte count, folate, and vitamin B12 of step iv) with their respective defined standards, wherein either a low level of folate or vitamin B12 and an elevated reticulocyte count are indicative of hemolytic anemia.

In some embodiments, the instructions further comprise comparing the reticulocyte count, folate, vitamin B12, and the hepatic function panel of step iv) with their respective defined standards, wherein: a) either a low level of folate or vitamin B12, an elevated reticulocyte count, and a normal hepatic function are indicative of a hematologic disease; or b) either a low level of folate or vitamin B12, an elevated reticulocyte count, and an abnormal hepatic function are indicative of anemia of chronic disease, optionally secondary to a liver disease, further optionally associated with alcohol.

In some embodiments, the instructions further comprise carrying out a methylmelonic acid test if the level of either folate or vitamin B12 is low but the reticulocyte count is normal.

In some instances, a blood sample (e.g., a whole blood sample or a peripheral blood sample) is obtained from an individual using a collection methodology that preserves one or more components of the blood. In some cases, one or more measurements are made within 72 hours, 48 hours, 24 hours, 12 hours, 6 hours, 4 hours, 2 hours, 1 hours, 45 minutes, 30 minutes, or less from time of collection. In some instances, the blood sample is further processed by centrifugation, lysis (e.g., vortex), homogenization, freeze-thaw methods, and/or filtration prior to undergoing subsequent testing utilizing one or more of the process described above.

In measuring the components included in a CBC analysis, the Hgb, MCV, and red blood cells may be directly determined, while the Hct and MCHC may be calculated based on indirect measures. An elevated MCHC can be the result of cellular loss of water leading to dehydration.

In some embodiments, a hematology analyzer is utilized to carry out one or more of the methods and tests described herein. In some instances, a hematology analyzer is utilized to carry out CBC measurements, a reticulocyte count test, and/or a hepatic function panel test. Exemplary hematology analyzers include, but are not limited to, a manual, semi-automated, or automated hematology analyzer, including but not limited to those described in, e.g., U.S. Pat. Nos. 5,017,497, 5,266,269, 5,378,633, 5,631,165, 5,812,419, 6,228,652, 6,524,858, 6,320,656, 7,324,194, and 7,981,681, and published U.S. Patent Applications US20080153170, US20080158561, US20080268494, US20110178716, 20110077871, and 20110070606. A number of models of hematology analyzers are commercially available, e.g., from Abbott Laboratories (Abbott Park, IL, United States)(e.g., the Cell-Dyn Sapphire); and Siemens Healthcare Diagnostics (Tarrytown, NY, United States) (e.g., the Advia 120 or 2120 automated hemanalyzer). Other manufacturers include Beckman Coulter, Inc. (Fullerton, CA, United States); TOA Medical Electronics Co., (Kobe, Japan); Constitution Medical (Boston, MA, United States); and HORIBA ABX Inc. (Irvine, CA, United States).

A reticulocyte count can also be carried out by a flow cytometer (e.g., fluorescence-activated cell sorting or FACS), an automated cell counter, or by a hemocytometer. Exemplary automated cell counters image-based cell counters, fluorescence-based cytometers, and coulter counters. Exemplary automated cell counter models are commercially available, e.g., from ThermoFisher Scientific (Waltham, MA, United States)(e.g., the Invitrogen Countess II Automated Cell Counter Invitrogen Countess II FL Automated Cell Counter); Olympus Life Science Solutions (Center Valley, PA, United States)(e.g., the Cell Counter model R1); and Bio-RAD (Hercules, CA, United States)(e.g., the TC20 cell counter). Hemocytometer is a manual cell counter and exemplary models include, but are not limited to, counters from ThermoFisher Scientific (Waltham, MA, United States) (e.g., the Hausser Scientific series of counting chambers and hemacytometers).

In some embodiments, a blood-gas analyzer (BGA) is used to determine, without limitations, blood gases (such as pH (acidity), carbon dioxide (measured as $pCO_2$— partial pressure of carbon dioxide), and/or oxygen (measured as $pO_2$— partial pressure of oxygen)); electrolytes (such as sodium ($Na^+$), potassium ($K^+$), Calcium ($Ca^{2+}$), and/or chloride (CI)); metabolites (such as glucose, lactate, blood urea nitrogen ("BUN"), and/or creatinine); and/or co-oximetry concentration measurements (such as total hemoglobin (tHb), reduced hemoglobin/deoxyhemoglobin (HH b), oxyhemoglobin ($O_2Hb$), saturated oxygen ($sO_2$), carboxyhemoglobin (COH b), methemoglobin (MetHb), fetal hemoglobin (HbF), and/or bilirubin. In some instances, a comprehensive metabolic panel and/or hepatic function panel are carried out on a blood-gas analyzer. Exemplary blood-gas analyzers include, but are not limited to, models from Radiometer America Inc. (Brea, CA, United States)(e.g., the ABL90 FLEX); Siemens Healthcare Diagnostics (Tarrytown, NY, United States)(e.g., the RAPIDPoint 500 Blood Gas Systems); Nova Biomedical (Waltham, MA, United States)(e.g., the Stat Profile Prime); Instrumentation Laboratory (San Diego, CA, United States)(e.g., the GEM Premier 4000 with Intelligent Quality Management (iQM)); Roche Diagnostics Corp. (Basel, Switzerland)(e.g., the cobas b 221); and Alere Inc. (Waltham, MA, United States)(e.g., the Enterprise Point of Care (epoc) Blood Analysis System).

In some embodiments, an enzymatic assay is used to detect and/or quantify one or more analytes from a test or test panel described herein. In some instances, the test or test panel comprise comprehensive metabolic panel (e.g., glucose and/or lactose), hepatic function panel, ferritin, folate, vitamin B12, reactive protein, or hemoglobinopathy evaluation tests. In one instance, products of enzymatic assays are quantified through changes in light absorptions. In such case, the enzymatic assays that are based on changes in light absorptions are referred to as colorimetric assays or luminescent assays. In another instance, a fluorometric assay is used to determine the presence and/or concentration of an analyte from a test or test panel described herein.

In some embodiments, an enzymatic assay is an enzyme immunoassay (EIA) (or enzyme-linked immunosorbent assay) for detecting and/or quantifying one or more analytes in a test or test panel described herein. In such instances, the test or test panels comprise comprehensive metabolic panel, hepatic function panel, c-reactive protein, or hemoglobinopathy evaluation.

Methods of detecting C-reactive protein (CRP) can comprise fluorescent immune chromatography, colloidal gold method, enzyme-linked immuno-adsorption, and apolipoprotein. CRP detection assays can further be divided into CRP assays that include qualitative, semi-quantitative and quantitative analysis; high sensitivity CRP (hsCRP) assays, and cardiac CRP (cCRP) assays. In some instances, a method for CRP detection is as described in PCT Application Publication No. WO2018/29885A1.

Methods for determining the level of ferritin can include an enzyme immunoassay. In some cases, the enzyme immunoassay includes a solid-phase enzyme immunoassay, a chemiluminescence enzyme immunoassay or a radioimmunoassay.

Methods for determining the level of vitamin B12 can include radioassay which measures the level of vitamin B12 in the sample; measuring the concentration of holotranscobalamin (the active component of vitamin B12) in the sample (see e.g., Clarke et al., *Clin. Chem.,* 53:963-970, 2007); an antibody test which check for antibodies; methylmalonic acid test which measures the presence of methylmalonic acid; or a Schilling test which may comprise an initial ingestion of a small amount of radioactive or labeled vitamin B-12 by an individual prior to checking the blood to determine whether the body has absorbed the radio-labeled vitamin B-12.

Methods for hemoglobinopathy evaluation can include chromatographic methods such as liquid chromatography (LC) method, gas chromatography (GC) method, and capillary electrophoresis (CE) method. In some instances, the LC is classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some cases, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography. Exemplary HPLC methods include, but are not limited to, hydrophilic interaction liquid chromatography (HILIC), electrostatic repulsion-hydrophilic interaction liquid chromatography (ERLIC) and reverse phase liquid chromatography (RPLC).

In some embodiments, the GC is coupled to a mass spectroscopy as a GC-MS method. Exemplary GC-MS methods include, but are not limited to, two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method.

Exemplary CE-MS methods include, but are not limited to, capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some instances, methods for hemoglobinopathy evaluation comprise isoelectric focusing (IEF) which separates proteins in a gel medium that has a pH gradient consisting of ampholytes (zwitterions); HPLC such as a cation exchange HPLC; cellulose acetate electrophoresis (or alkaline electrophoresis); citrate agar electrophoresis (which is carried out under an acidic environment); alkaline globin chain electrophoresis (in which the hemoglobin molecules can be separated into their respective globin chain components and heme groups in the presence of 2-mercaptoethanol and urea); or capillary zone electrophoresis.

In some embodiments, methods for hemoglobinopathy evaluation also comprise a molecular method, such as for example, polymerase chain reaction (PCR) based assays, restriction fragment length polymorphism (RFLP) (e.g., utilizing recognition sequences of restriction enzymes that correspond to either normal allele or mutated allele of a gene to determine whether a mutation is present within the beta-globin B (HBB) gene), allelic discrimination (AD) with real-time PCR, or DNA sequencing (e.g., Sanger sequencing).

In some embodiments, additional methodologies are also utilized to detect and/or to quantify one or more analytes in a test or test panel described herein. In some instances, the additional methodologies include a nuclear magnetic resonance (NMR) method. In some embodiments, the NMR method includes one dimensional (1D) NMR methods, two dimensional (2D) NMR methods, solid state NMR methods and NMR chromatography. Exemplary 1D NMR methods include $^{1}$Hydrogen, $^{13}$Carbon, $^{15}$Nitrogen, $^{17}$Oxygen, $^{19}$Fluorine, $^{3}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR chromatography include diffusion ordered spectroscopy (DOSY), DOSY-TOCSY and DOSY-HSQC.

In some embodiments, the system comprises one or more computing devices that are integrated into, or forms part of, a multi-computing device. In alternative embodiments, the system comprises separate computing devices.

In some instances, the system comprises a memory, a display, and at least one processor coupled to the memory programmed with executable instructions. In some instances, the executable instructions or programmings can be provided in a physical storage or transmission medium. Examples of storage media that are computer-readable include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network. In some embodiments, the processes described herein are automatically executed each time a sample is run.

As utilized herein, a computing device can encompass various forms of digital computers, including, e.g., laptops, desktops, workstations, personal digital assistants, servers, blade servers, mainframes, and other appropriate computers; and various forms of mobile devices, including, e.g., personal digital assistants, cellular telephones, smartphones, and other similar computing devices.

In some instances, an exemplary computing device includes a processor, a memory, a storage device, a high-speed user interface connecting to the memory and high-speed expansion ports, and a low speed user interface connecting to a low speed bus and the storage device. Each of the components can be interconnected using various busses, and can be mounted on a common motherboard or in other manners as appropriate. The processor can process instructions for execution within the computing device, including instructions stored in the memory or on a storage device to display graphical information for a GUI on an external input/output device, including, e.g., a display coupled to the high speed user interface. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory can store information within the computing device. In one implementation, the memory is a volatile memory unit or units. In another implementation, the memory is a non-volatile memory unit or units. The memory also can be another form of computer-readable medium, including, e.g., a magnetic or optical disk.

The storage device can be capable of providing mass storage for the computing device. In one implementation, the storage device can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product also can contain instructions that, when executed, perform one or more methods, including, e.g., those described above. The information carrier is a computer- or machine-readable medium, including, e.g., memory, storage device, memory on processor, and the like.

The high-speed controller can manage bandwidth-intensive operations for the computing device, while low speed controller manages lower bandwidth-intensive operations. Such allocation of functions is an example only. In one implementation, the high-speed controller is coupled to the memory, the display (e.g., through a graphics processor or accelerator), and to high-speed expansion ports, which can accept various expansion cards (not shown). In the implementation, the low-speed controller can be coupled to the storage device and the low-speed expansion port. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

The computing device can be implemented in a number of different forms, such as for example, as a standard server, or multiple times in a group of such servers. It also can be implemented as part of a rack server system. In addition or as an alternative, it can be implemented in a personal computer including, e.g., a laptop computer. In some examples, components from the computing device can be combined with other components in, e.g., a mobile device. Each of such devices can contain one or more of the computing device and an entire system can be made up of multiple computing devices communicating with each other.

The display can be, for example, a TFT LCD (Thin-Film-Transistor Liquid Crystal Display) or an OLED (Organic Light Emitting Diode) display, or other appropriate display technology. The display user interface can comprise appropriate circuitry for driving display to present graphical and other information to a user. Control user interface can receive commands from a user and convert them for submission to the processor. In addition, an external user interface can communicate with the processor, so as to enable near area communication of the computing device with other devices. External user interface can provide, for example, for wired communication in some implementations, or for wireless communication in other implementations, and multiple user interfaces also can be used.

In some instances, the computing device can communicate wirelessly through a communication user interface, which can include digital signal processing circuitry where necessary. The communication user interface can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver. In addition, short-range communication can occur, including, e.g., using a Bluetooth®, WiFi, or other such transceiver. In addition, GPS (Global Positioning System) receiver module can provide additional navigation- and location-related wireless data to the computing device, which can be used as appropriate by applications running on the computing device.

In some cases, the computing device can also communicate audibly using an audio codec, which can receive spoken information from a user and convert it to usable digital information. Audio codec can likewise generate audible sound for a user, including, e.g., through a speaker, e.g., in a handset unit of the computing device. Such sound can include sound from voice telephone calls, can include recorded sound (e.g., voice messages, music files, and the like) and also can include sound generated by applications operating on the computing device.

Various implementations of the systems and processes described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and processes described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and processes described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Methods of Treatment

Disclosed herein, in additional embodiments, are methods of treating an underlying cause of anemia in an individual in need thereof. Anemia as described herein generally relates to a condition in which there is low hemoglobin, low hematocrit, low packed cell volume, or reduced oxygen-carrying capacity of red blood cells to tissues. In some instances, anemic conditions include, but are not limited to, hemolytic anemias (including but not limited to thalassemias, hereditary spherocytosis, hereditary elliptocytosis, hereditary xerocytosis, glucose-6-phosphate dehydrogenase deficiency (G6PD), pyruvate kinase deficiency, immune hemolytic anemia, alloimmune hemolytic anemia, drug-induced hemolytic anemia, mechanical hemolytic anemias, and paroxysmal nocturnal hemoglobinuria), anemia of chronic disease (wherein the underlying condition can be, for example, autoimmune disorders (such as, for example Crohn disease, systemic lupus erythematosus, rheumatoid arthritis and ulcerative colitis), neoplastic disorders including cancer (such as, for example lymphoma and Hodgkin disease), long-term infections (such as, for example bacterial, viral, and fungal infections), rheumatoid arthritis, ulcerative colitis, Hodgkin disease, metabolic syndrome, diabetes (for example, type 2 diabetes), and other causes of chronic inflammation), anemia, aplastic anemias (including but not limited to congenital hypoplastic anemia, Diamond-Blackfan anemia and Fanconi anemia), iron deficiency anemia (IDA), anemias of abnormal RBC size (including but not limited to megaloblastic anemia and microcytic anemia), vitamin deficiency anemias (including but not limited to pernicious anemia) anemia of RBC mutation (including but not limited to thalassemia, sideroblastic anemia and sickle cell anemia).

An anemic condition can be classified as normochromic, which is generally understood to be an anemic condition in which the concentration of hemoglobin in the RBCs is not pathological, but there are insufficient numbers of RBCs. An anemic condition can be classified as normocytic, which is generally understood to be an anemic condition in which RBCs are not abnormal in size. Normocytic, normochromic anemias include anemia of chronic disease (ACD) and hemolytic anemia.

Anemia associated with premature RBC destruction is generally referred to as hemolytic anemia. Some forms of hemolytic anemia are inherited and others are acquired.

Hemolytic anemia is associated with conditions including but not limited to autoimmune disorders, infections (such as, for example, hepatitis), cell proliferation disorders (such as, for example, leukemia and lymphoma), certain medications, sickle cell anemia, and Wiskott-Aldrich syndrome. In some instances, hemolytic anemia is divided into inherited hemolytic anemia and acquired hemolytic anemia. In some cases, the inherited hemolytic anemia comprises sickle cell anemia, thalassemias, hereditary xerocytosis, hereditary spherocytosis, hereditary elliptocytosis (ovalocytosis), glucose-6-phosphate dehydrogenase (G6PD) deficiency, and pyruvate kinase deficiency. In some cases, the acquired hemolytic anemia comprises immune hemolytic anemia, mechanical hemolytic anemias, paroxysmal nocturnal hemoglobinuria, pathogen-induced acquired hemolytic anemia, and chemical-induced acquired hemolytic anemia. Additional types of immune hemolytic anemia can comprise autoimmune hemolytic anemia (AIHA), alloimmune hemolytic anemia, and drug-induced hemolytic anemia. The pathogen-induced acquired hemolytic anemia can comprise one or more pathogens that damage red blood cells, optionally comprising protozoans from the genus *Plasmodium* (optionally comprising *P. falciparum, P. malariae, P. ovale*, and *P. vivax*) or bacteria from the genus *Borrelia* (optionally comprising *B. burgdorferi, B. mayonii, B. afzelii*, and *B. garinii*). The chemical-induced acquired hemolytic anemia can comprise one or more chemicals that damage red blood cells, optionally comprising toxic chemicals or venom (e.g., a snake venom).

RBCs can be removed from circulation due to senescence. Without wishing to be bound by theory, RBCs undergo age-dependent alterations, which may include a decline in metabolic activity, a progressive cell shape transformation, membrane remodeling, oxidative injury, microvesiculation and exposure of surface removal markers. These modifications may trigger phagocytosis by macrophages, in which RBCs are destroyed. It is thought that the protease calpain may become activated in the process, which may be triggered by an increase of cytosolic calcium. Elevated rates of RBC destruction may lead to an anemic condition.

Anemia of chronic disease (ACD), also called anemia of inflammation and inflammatory anemia, is anemia associated with a chronic underlying condition. An underlying condition may suppress production of red blood cells in the bone marrow, may decrease the lifespan of red blood cells, or may create problems with how the body uses iron. Generally, ACD develops and presents slowly, with mild or no symptoms.

Inflammation may play a role in the pathogenesis of ACD. Without wishing to be bound by theory, it is thought that inflammatory cytokines present in many chronic diseases, which both lower red blood cell production and raise premature breakdown of senescent cells, leading to anemia. Thus, cytokines and cells of the reticuloendothelial system affect iron homeostasis, production of erythroid progenitor cells, the production of erythropoietin, and the life span of RBCs, each of which can contribute to an anemic condition.

Further, ACD may be associated with abnormal homeostasis of iron in the body. Increased uptake and retention of iron within cells of the reticuloendothelial system may be observed. In subjects having ACD, ferritin levels may be elevated.

Underlying conditions of ACD include those associated with hemolytic anemia, include, but are not limited to, autoimmune disorders (such as, for example Crohn disease, systemic lupus erythematosus, rheumatoid arthritis and ulcerative colitis), neoplastic disorders including cancer (such as, for example solid tumor or a hematologic disease, optionally lymphoma (such as a B-cell lymphoma or a T-cell lymphoma), Hodgkin's disease, or non-Hodgkin's disease), long-term infections (such as, for example bacterial, viral, and fungal infections), rheumatoid arthritis, ulcerative colitis, metabolic syndrome, diabetes (for example, type 2 diabetes), and other causes of chronic inflammation.

Where the underlying condition of ACD is a neoplastic disorder, erythropoiesis can be affected by the infiltration of tumor cells into bone marrow. Tumor cells can produce proinflammatory cytokines and free radicals that damage erythroid progenitor cells. Bleeding episodes, vitamin deficiencies, hypersplenism, autoimmune hemolysis, renal dysfunction, and radio- and chemotherapeutic interventions can also aggravate anemia.

Where the underlying condition is an infection, ACD can be classified as anemia of chronic infection (ACI). Erythropoiesis can be affected by the infiltration of microorganisms, as seen in various infections, including human immunodeficiency virus (HIV) infection, hepatitis C, and malaria.

Anemia with chronic kidney disease shares some characteristics of anemia of chronic disease. Decrease in the production of erythropoietin, due to renal insufficiency and accumulating toxins, may contribute. In patients with end-stage renal disease, chronic immune activation can arise from contact activation of immune cells by dialysis membranes and/or from frequent episodes of infection.

Aplastic anemia is associated with low RBC production.

Iron deficiency anemia is associated with a deficiency in iron stores such that erythropoiesis is inadequate.

In some instances, the serum ferritin level is elevated, compared to a defined standard, and the elevated ferritin level signals an acute phase reaction or response by the body prior to a full activation of the immune response in response to an infection or trauma. The acute phase reaction or response comprises production of select proteins, termed acute phase proteins (APPs), which can be either elevated (termed positive APPs), or decreased (termed negative APPs). Measurement of these APPs provide additional input in the cause and/or type of infection and/or trauma. In some cases, the positive APPs include CRP, $\alpha$-1-antichymotrypsin (ACT), AGP, also known as orosomucoid, serum amyloid A (SAA), fibrinogen, haptoglobin, caeruloplasmin and ferritin. In some cases, the negative APPs include transferrin, albumin, transthyretin and retinol binding protein (RBP). In some instances, the serum ferritin level is elevated, compared to a defined standard, and the elevated ferritin level signals a chronic phase reaction or response.

Sickle cell anemia may be caused by a mutation which results in mutant sickle hemoglobin. Sideroblastic anemias are a group of disorders with the common features of mitochondrial iron accumulation in bone marrow, ineffective erythropoiesis, and increased tissue iron levels.

Fanconi anemia refers to a rare genetic disorder associated with a high frequency of hematological abnormalities and congenital anomalies.

Vitamin deficiency anemia refers to a lack of healthy red blood cells caused by lower than normal amounts of certain vitamins. Vitamins linked to vitamin deficiency anemia include folate, vitamin B-1, or Vitamin C.

Microcytic anemias are characterized by the production of red blood cells that are smaller than normal. In some instances, microcytic anemia is caused by one or more of a lack of globin product (thalassemia), restricted iron delivery to a heme group of hemoglobin, and defects in the synthesis of the heme group. Exemplary microcytic anemias include, but are not limited to, iron deficiency anemia (IDA), thalassemia trait (TT), and anemia of chronic disease (ACD).

Normocytic anemias are characterized by the production of red blood cells that fall within the normal range but with either normal or low level of MCHC and/or decreased level of Hb level. Exemplary normocytic anemias include, but are not limited to, nutritional anemia (e.g., IDA, cobalamin and/or folate deficiency), anemia of renal insufficiency, hemolytic anemia, ACD, anemia associated with a primary bone marrow disorder (e.g., bone marrow aplasia such as idiopathic, PNH, or Fanconi syndrome; pure red cell aplasia such as acquired, congenital, or Diamond-Blackfan syndrome; myelodysplastic syndrome; extrinsic cause such as drugs, toxins, radiation, pathogens, immune-mediated, or bone marrow infiltration).

Macrocytic anemias are characterized by the production of red blood cells that are larger than the normal range of RBCs. Exemplary macrocytic anemias include, but are not limited to, drug induced anemia (e.g., hydroxyurea, zidovudine, methotrexate), nutritional deficiencies (e.g., vitamin B12, folate, and/or copper), drug-induced hemolytic anemia, dyserythropoiesis, myelodysplastic syndrome, hematologic disorder (e.g., clonal hematologic disorder or hereditary hematologic disorder), liver disease, genetic disease (e.g., Down syndrome), or pulmonary disease (e.g., chronic obstructive pulmonary disease).

In some embodiments, a treatment for hemolytic anemia comprises blood transfusion, plasmapheresis, blood and/or marrow stem cell transplant, surgery, a therapeutic agent, or a combination thereof. In some cases, exemplary treatments for a hemolytic anemia comprise steroids such as beclomethasone, betamethasone, budesonide, cortisone, dexamethasone, hydrocortisone, methylprednisolone, prednisolone, prednisone, or triamcinolone; rituximab; folic acid; azathioprine; cyclophosphamide; mycophenolate; cyclosporine; danazol; alemtuzumab; sirolimus; or splenectomy.

In some embodiments, a treatment for iron deficiency anemia (IDA) comprises administration of soluble iron (e.g., iron supplements). Exemplary drugs include, but are not limited to, iron dextran, iron sumalate, polysaccharide iron, ferrus fumarate, carbonyl iron, ferrous asparto glycinate, heme iron polypeptide, and ferrus bisglycinate, which can be co-administered with other medicaments such as androgen hormones, folic acid, vitamin B12, vitamin C, succinic acid, niacin, pyridoxine, riboflavin, biotin, thiamine, calcium formate, Aminoxin, Anadrol-50, Chromagen Forte, Epoetin alfa, Epogen, Fe C Tab Plus, FeRiva, FeRivaFA, Ferocon, Ferotrin, Ferralet 90, Ferrex 28, Ferrogels Forte, FoliTab 500, Fumatinic, Hematogen Forte, Hemetab, Integra Plus, Irospan 42/6, Lenalidomide, Maxaron Forte, Myferon 150 Forte, MyKidz Iron, NovaFerrum, Oxymetholone, Procrit, Proferrin-Forte, Pyridoxine, Repliva 21/7, Revlimid, or Tricon.

In some embodiments, a treatment for hemoglobinopathy is a supportive treatment instead of a curative treatment. In some cases, stem-cell transplantation is utilized for the treatment of several forms of thalassemia. Blood transfusion, optionally in combination with one or more drugs such as analgesics, antibiotics, ACE inhibitors and hydroxyurea can be utilized for the treatment of hemoglobinopathy.

In some embodiments, a treatment for anemia of chronic disease (ACD) comprises a steroid or a nonsteroidal anti-inflammatory agent for the treatment of an underlying inflammation, antibiotics for an underlying pathogenic infection, or a cancer treatment. Exemplary steroids comprise beclomethasone, betamethasone, budesonide, cortisone, dexamethasone, hydrocortisone, methylprednisolone, prednisolone, prednisone, or triamcinolone. Exemplary nonsteroidal anti-inflammatory agent (NSAIDs) comprise aspirin, celecoxib, diclofenac, diflunisal, etodolac, ibuprofen, indomethacin, ketoprofen, ketorolac, nabumetone, naproxen, oxaprozin, piroxicam, salsalate, sulindac, or tolmetin.

In some instances, antibiotic classes comprise penicillins, tetracyclines, cephalosporins, quinolones, lincomycins, macrolides, sulfonamides, glycopeptides, aminoglycosides, and carbapenems. Exemplary antibiotics include, but are not limited to, amoxicillin, doxycycline, cephalexin, ciprofloxacin, metronidazole, azithromycin, sulfamethoxazole and trimethoprim, amoxicillin and clavulanate, and levofloxacin.

In some instances, cancer therapies comprise chemotherapeutic agents, immunotherapeutic agents, targeted therapies, radiation therapies, or a combination thereof. Exemplary therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some embodiments, disclosed herein is a method of treating an underlying cause of anemia in an individual in need thereof, comprising: (a) assessing a hemoglobin level, mean corpuscular hemoglobin concentration (MCHC), and mean corpuscular volume (MCV) from a blood sample obtained from the individual; (b) comparing the hemoglobin level, MCHC level, and MCV value to a defined standard for hemoglobin level, MCHC, and MCV; (c) based on step b), carrying out one or more additional tests selected from: (i) a reticulocyte count if the MCHC level is elevated compared to the defined standard for MCHC; (ii) a reticulocyte count, ferritin level, and hemoglobinopathy evaluation if the hemoglobin level is lower than the defined standard for hemoglobin level, the MCV value is lower than the defined standard for MCV, and the MCHC level is normal or lower than the defined standard for MCHC; (iii) a reticulocyte count, ferritin level, C-reactive protein (CRP), and comprehensive metabolic panel (CMP) if the hemoglobin level is lower than the defined standard for hemoglobin level, the MCV value is normal compared to the defined standard for MCV, and the MCHC level is normal or lower than the defined standard for MCHC; or (iv) a reticulocyte count, folate, vitamin B12, and hepatic function panel if the hemoglobin level is lower than the defined standard for hemoglobin level, and the MCV value is elevated by at least about 10% compared to the defined standard for MCV; and (d) based on step c), administering a treatment to the individual, thereby treating the underlying cause of anemia.

In some instances, step ci) further comprises comparing the reticulocyte count with a defined standard, wherein an elevated reticulocyte count is indicative of hemolytic anemia. In some cases, a subsequent genetic testing is required to further evaluate an underlying case of hemolytic anemia.

In some instances, step cii) further comprises comparing the ferritin level with a defined standard, wherein a reduced level of ferritin is indicative of iron deficiency.

In some instances, step cii) further comprises comparing the reticulocyte count, ferritin level, and hemoglobinopathy evaluation with their respective defined standards, wherein: a) a normal or elevated level of ferritin, a normal hemoglobinopathy evaluation and a normal reticulocyte count are indicative of anemia of chronic disease; b) a normal or elevated level of ferritin, a normal hemoglobinopathy evaluation, and an elevated reticulocyte count are indicative of hemolytic anemia; or c) a normal or elevated level of ferritin, an abnormal hemoglobinopathy evaluation, and a normal or elevated reticulocyte count are indicative of anemia of a hemoglobinopathy.

In some instances, step ciii) further comprises comparing the ferritin level with a defined standard, wherein a reduced level of ferritin is indicative of iron deficiency, optionally early iron deficiency.

In some instances, step ciii) further comprises comparing the ferritin level with a defined standard, wherein an elevated level of ferritin is indicative of an acute phase reaction.

In some instances, step ciii) further comprises comparing the ferritin level, CRP, CMP, and the reticulocyte count with their respective defined standards, wherein: a) a normal level of ferritin and an elevated reticulocyte count are indicative of hemolytic anemia or gastrointestinal bleeding; b) a normal level of ferritin, a low or normal reticulocyte count, an elevated level of CRP, and an abnormal or normal CMP are indicative of anemia of chronic disease (ACD); or c) a normal level of ferritin, a normal reticulocyte count, and a normal level of CRP are indicative of a chronic disease or dimorphic anemia.

In some instances, step civ) further comprises comparing folate and vitamin B12 with their respective defined standards, wherein either a low level of folate or vitamin B12 is indicative of folate or vitamin B12 deficiency. In some cases, a methylmelonic acid test is further carried out to confirm a vitamin B12 deficiency.

In some instances, step civ) further comprises comparing the reticulocyte count, folate, and vitamin B12 with their respective defined standards, wherein either a low level of folate or vitamin B12 and an elevated reticulocyte count are indicative of hemolytic anemia.

In some instances, step civ) further comprises comparing the reticulocyte count, folate, vitamin B12, and the hepatic function panel with their respective defined standards, wherein: a) either a low level of folate or vitamin B12, an elevated reticulocyte count, and a normal hepatic function are indicative of a hematologic disease; or b) either a low level of folate or vitamin B12, an elevated reticulocyte count, and an abnormal hepatic function are indicative of anemia of chronic disease, optionally secondary to a liver disease, further optionally associated with alcohol.

In some embodiments, also disclosed herein is a method of treating an underlying cause of microcytic anemia in an individual in need thereof, comprising: assessing a reticulocyte count, ferritin level, and a hemoglobinopathy evaluation from a blood sample obtained from the individual; comparing the reticulocyte count and ferritin level with their respective defined standard; and (i) administering to the individual a soluble form of iron if the ferritin level is lower than the defined standard; or (ii) administering to the individual a treatment for anemia of chronic disease if the level of ferritin is normal or elevated compared to the defined standard, the reticulocyte count is normal compared to the defined standard, and the hemoglobinopathy evaluation is normal; or (iii) administering to the individual a treatment for hemolytic anemia if the level of ferritin is normal or elevated compared to the defined standard, the reticulocyte count is elevated compared to the defined standard, and the hemoglobinopathy evaluation is normal; or (iv) administering to the individual a treatment for hemoglobinopathy if the level of ferritin is normal or elevated compared to the defined standard, the reticulocyte count is normal or elevated compared to the defined standard, and the hemoglobinopathy evaluation is abnormal.

In some embodiments, further disclosed herein is a method of treating an underlying cause of normocytic anemia in an individual in need thereof, comprising: assessing a reticulocyte count, ferritin level, C-reactive protein (CRP), and comprehensive metabolic panel (CMP) from a blood sample obtained from the individual; comparing the reticulocyte count, ferritin level, CRP level, and CMP with their respective defined standard; and (i) administering to the individual a soluble form of iron if the ferritin level is lower than the defined standard; or (ii) carrying out an additional evaluation of the individual if the ferritin level is elevated compared to the defined standard; or (iii) administering to the individual a treatment for hemolytic anemia or gastrointestinal bleeding if the ferritin level is normal compared to the defined standard and the reticulocyte count is elevated compared to the defined standard; or (iv) administering to the individual a treatment for anemia of chronic disease (ACD) if the ferritin level is normal compared to the defined standard, the reticulocyte count is elevated compared to the defined standard, and the CMP is normal or abnormal; or (v) administering to the individual a treatment for a chronic disease or dimorphic anemia if the ferritin level is normal compared to the defined standard, the reticulocyte count is normal compared to the defined standard, and the CRP is normal.

In some embodiments, additionally disclosed herein is a method of treating an underlying cause of macrocytic anemia in an individual in need thereof, comprising: assessing a reticulocyte count, folate, vitamin B12, and hepatic function panel from a blood sample obtained from the individual; comparing the reticulocyte count, folate, vitamin B12, and hepatic function panel with their respective defined standard; and (i) administering to the individual a folate supplement or a vitamin B12 supplement if either the level of folate or vitamin B12 is low compared to the defined standard; or (ii) administering to the individual a treatment for hemolytic anemia if the level of folate or vitamin B12 is low compared to the defined standard and the reticulocyte count is elevated compared to the defined standard; or (iii) administering to the individual a treatment for a hematologic disease if the level of folate or vitamin B12 is low compared to the defined standard, the reticulocyte count is elevated compared to the defined standard, and the hepatic function is normal compared to a defined standard; or (iv) administering to the individual a treatment for anemia of chronic disease if the level of folate or vitamin B12 is low compared to the defined standard, the reticulocyte count is elevated compared to the defined standard, and the hepatic function is abnormal compared to a defined standard.

In some instances, the hemolytic anemia comprises an inherited hemolytic anemia or an acquired hemolytic anemia. In some cases, the inherited hemolytic anemia comprises sickle cell anemia, thalassemias, hereditary xerocytosis, hereditary spherocytosis, hereditary elliptocytosis (ovalocytosis), glucose-6-phosphate dehydrogenase (G6PD) deficiency, and pyruvate kinase deficiency. In some cases, the acquired hemolytic anemia comprises immune hemolytic anemia, mechanical hemolytic anemias, paroxysmal nocturnal hemoglobinuria, pathogen-induced acquired hemolytic anemia, and chemical-induced acquired hemolytic anemia. In some cases, the immune hemolytic anemia comprises autoimmune hemolytic anemia (AIHA), alloimmune hemolytic anemia, and drug-induced hemolytic anemia. In some cases, the pathogen-induced acquired hemolytic anemia comprises one or more pathogens that damage red blood cells, optionally comprising protozoans from the genus *Plasmodium* or bacteria from the genus *Borrelia*. In some cases, *Plasmodium* comprises *P. falciparum, P. malariae, P. ovale*, and *P. vivax*. In some cases, *Borrelia* comprises *B. burgdorferi, B. mayonii, B. afzelii*, and *B. garinii*. In some cases, the chemical-induced acquired hemolytic anemia comprises one or more chemicals that damage red blood cells, optionally comprising toxic chemicals or venom.

In some instances, the hematologic disease comprises myelodysplasia.

In some instances, a treatment for hemolytic anemia comprises blood transfusion, plasmapheresis, blood and/or marrow stem cell transplant, surgery, a therapeutic agent, or a combination thereof.

In some instances, a treatment for iron deficiency anemia (IDA) comprises administration of soluble iron.

In some instances, a treatment for anemia of chronic disease (ACD) comprises a steroid or a nonsteroidal anti-inflammatory agent for the treatment of an underlying inflammation, antibiotics for an underlying pathogenic infection, or a cancer treatment.

In some embodiments, a defined standard for MCHC is from about 32% to about 36%, from about 33% to about 36%, from about 33% to about 35%, or from about 32% to about 35%. In some instances, an elevated MCHC level is greater than about 35% or greater than about 36%. In some instances, a decreased or low MCHC level is less than about 33% or less than about 32%.

In some embodiments, a defined standard for MCHC is from about 32 g/dL to about 36 g/dL, from about 33 g/dL to about 36 g/dL, or from about 33.4 g/dL to about 35.5 g/dL. In some instances, an elevated MCHC level is greater than about 35 g/dL, greater than about 35.5 g/dL, or greater than about 36 g/dL. In some instances, a decreased or low MCHC level is less than about 33.4 g/dL, less than about 33 g/dL, or less than about 32 g/dL.

In some embodiments, a defined standard for hemoglobin level for men is from about 13 mg/L to about 17.5 mg/L or from about 13.2 mg/L to about 17.5 mg/L. In some instances, a decreased hemoglobin level for men is less than about 13.2 mg/L or less than about 13 mg/L.

In some embodiments, a defined standard for hemoglobin level for women is from about 11 mg/L to about 15.3 mg/L, from about 11.6 mg/L to about 15 mg/L, from about 11.7 mg/L to about 15 mg/L, or from about 12 mg/L to about 15 mg/L. In some instances, a decreased hemoglobin level for women is less than about 11 mg/L, less than about 11.6 mg/L, less than about 11.7 mg/L, or less than about 12 mg/L.

In some embodiments, a defined standard for MCV is from about 80 fL to about 100 fL, from about 80 fL to about 98 fL, or from about 80 fL to about 96 fL. In some instances, an elevated MCV value is greater than about 96 fL, greater than about 97 fL, greater than about 98 fL, greater than about 99 fL, or greater than 100 fL. In some instances, a reduced or low MCV value is less than about 80 fL or less than about 79 fL.

In some embodiments, a defined standard for the reticulocyte count is from about 0.5% to about 2.5%, from about 0.5% to about 2%, or from about 0.5% to about 1.5%. In some instances, an elevated reticulocyte count is greater than 1.5%, greater than 2%, or greater than 2.5%.

In some embodiments, a defined standard for the reticulocyte count is from about $10\times10^9$ to about $110\times10^9$ RBCs/L, from about $50\times10^9$ to about $100\times10^9$ RBCs/L, or from about $50\times10^9$ to about $150\times10^9$ RBCs/L. In some instances, an elevated reticulocyte count is greater than $100\times10^9$ RBCs/L, greater than $110\times10^9$ RBCs/L, or greater than $150\times10^9$ RBCs/L.

In some embodiments, a defined standard for ferritin for men is from about 12 to about 300 ng/mL, from about 20 to about 300 ng/mL, or from about 20 to about 250 ng/mL. In some instances, an elevated level of ferritin for men is greater than about 250 ng/mL or greater than about 300 ng/mL.

In some embodiments, a defined standard for ferritin for women is from about 12 to about 270 ng/mL, from about 12 to about 263 ng/mL, from about 20 to about 200 ng/mL, from about 12 to about 150 ng/mL, or from about 10 to about 120 ng/mL. In some instances, an elevated level of ferritin for women is greater than about 120 ng/mL, greater than about 150 ng/mL, greater than about 200 ng/mL, greater than about 263 ng/mL, or greater than about 270 ng/mL.

In some embodiments, a decreased or low level of ferritin is less than about 20 ng/mL, less than about 12 ng/mL, or less than 10 ng/mL. In some cases, the decreased or low level of ferritin is applicable to both men and women.

In some embodiments, a defined standard for CRP is from about 0.2 mg/L to about 6.1 mg/L, from about 0.2 mg/L to about 6 mg/L, or from about 0.2 mg/L to about 5 mg/L. In some instances, an elevated CRP level is greater than about 5 mg/L, greater than about 6 mg/L, or greater than about 6.2 mg/L.

In some embodiments, a defined standard for folate conducted on a blood plasma is from about 2 ng/mL to about 10 ng/mL or from about 2.7 ng/mL to about 17 ng/mL. In some instances, a defined standard for folate conducted on RBCs is from about 140 ng/mL to about 960 ng/mL.

In some embodiments, a defined standard for vitamin B12 is from about 200 to about 900 ng/mL.

In some embodiments, the hepatic function panel comprises testing the level of total protein, albumin, bilirubin, alkaline phosphatase (ALP), alanine transaminase (ALT), and aspartate aminotransferase (AST). In some instances, a defined standard for ALP is from about 25 IU/L to about 160 IU/L or from about 40 IU/L to about 129 IU/L. In some instances, a defined standard for ALT is from about 0 IU/L to about 55 IU/L or from about 7 IU/L to about 55 IU/L. In some instances, a defined standard for AST is from about 0 IU/L to about 40 IU/L or from about 8 IU/L to about 48 IU/L.

Definitions

Unless defined otherwise, all technical and scientific terms used herein have the meaning commonly understood by a person skilled in the art to which this disclosure belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

The section headings used herein are for organizational purposes only and are not to be construed as limiting the subject matter described.

As used in the description of the invention and the appended claims, the singular forms “a”, “an” and “the” are used interchangeably and intended to include the plural forms as well and fall within each meaning, unless the context clearly indicates otherwise. Also, as used herein, “and/or” refers to and encompasses any and all possible combinations of one or more of the listed items, as well as the lack of combinations when interpreted in the alternative (“or”).

As used herein, the term “about” will be understood by persons of ordinary skill in the art and will vary to some extent depending upon the context in which it is used. If there are uses of the term which are not clear to persons of ordinary skill in the art given the context in which it is used, “about” will mean up to plus or minus 10% of the particular term.

As used herein, the term “administration” of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

As used herein, the term “automated” indicates that the process is carried out without intermittent instruction regarding how the process should proceed. In other words, once a physician (i.e., a primary care physician) requests or orders a disclosed method or process, the steps are carried out to completion without the need for further requests or order to proceed with the next testing step. Thus, the disclosed processes do not have to be carried out in a single machine without human interaction, although in some embodiments this may occur. In some embodiments, the individual testing steps (e.g., determining ferritin levels, determining reticulocyte count, assessing C-reactive protein, etc.) may involve human interaction, such as handling by a laboratory technician, but the process is nevertheless “automated” in that the individual handling the sample proceeds with the required test without new, direct, or intermittent instruction from a physician.

As used herein, the term “comprising” is intended to mean that the compositions and methods include the recited elements, but not excluding others. “Consisting essentially of” when used to define compositions and methods, shall mean excluding other elements of any essential significance to the composition or method. “Consisting of” shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

In some instances, a "normal range" may be also referred to as a "defined standard." For example, a normal range for a MCHC, MCV, or MCH value can also be referred to as a defined standard.

As used herein, "optional" or "optionally" means that the subsequently described event or circumstance may or may not occur, and that the description includes instances where said event or circumstance occurs and instances where it does not.

As used herein, the phrase "therapeutically effective amount" means that drug dosage or plasma concentration in a subject that provides the specific pharmacological effect for which the drug is administered in a subject in need of such treatment, i.e. to reduce, ameliorate, or eliminate the symptoms or effects of a anemia and/or its underlying cause (e.g., a hematological disease or mutation, anemia from a chronic disease, hemolytic anemia, etc.). It is emphasized that a therapeutically effective amount or therapeutic level of a drug will not always be effective in treating the conditions/diseases described herein, even though such dosage is deemed to be a therapeutically effective amount by those of skill in the art. The therapeutically effective amount may vary based on the route of administration and dosage form, the age and weight of the subject, and/or the subject's condition, including the type and severity of an individual's anemia or the underlying cause of the anemia, among other factors.

The terms "treatment" or "treating" as used herein with refer to reducing, ameliorating or eliminating one or more symptoms or effects of anemia or its underlying cause.

The preceding disclosure and following examples are provided to aid the reader in understanding the patent application and are not admitted to describe or constitute prior art thereto.

EXAMPLES

These examples are provided for illustrative purposes only and not to limit the scope of the claims provided herein.

Example 1

Anemia is the most common blood disorder affecting more than 3 million Americans. An anemia profile is a diagnostic tool to identify various anemias based on a patient' symptoms and clinical lab results. This example provides a comprehensive reflex testing for a primary care physician (PCP) to improve patient care outcome. Based on the MCV results, anemias can be classified morphologically as microcytic (low MCV), normocytic (normal MCV), or macrocytic (high MCV).

The results of the MCV will determine the standardized cascade of reflex tests. The goal of the standardized cascade of reflex tests is to initiate appropriate testing all at once based on the Hb level, MCHC, and MCV and which will mitigate the patient's need to return for additional testing and/or to decrease turn around to diagnosis. Table 1 illustrates the standardized reflex testing cascades. Also see FIG. 1B which illustrates the anemia algorithm associated with the standardized reflex test cascades.

Inclusion criteria for this experiment include patients who have not been evaluated for iron deficiency in the past 3 months.

Exclusion criteria include patients currently under evaluation or treatment for iron deficiency or who have a known personal or family history of a red blood cell disorder. The exclusion criteria also include patients suspected of having aplastic anemia.

TABLE 1

| Blood Parameters | Reflex Test Panel | Test Name |
|---|---|---|
| Elevated MCHC | Cascade 1 | Reticulocyte Count |
| Microcytic (low MCV); low or normal MCHC; low Hb level | Cascade 2 | Reticulocyte Count; Hemoglobinopathy evaluation; ferritin |
| Normocytic (normal MCV); low or normal MCHC; low Hb level | Cascade 3 | Reticulocyte Count; Comprehensive metabolic panel (CMP); C-reactive Protein (CRP); Ferritin |
| Macrocytic (high MCV; elevated by at least 10%); low Hb level | Cascade 4 | Reticulocyte Count; Folate, serum; Vitamin B12; Hepatic function panel |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of detecting a cause of anemia selected from the group consisting of: sickle cell anemia, hereditary spherocytosis, hemolytic anemia, alpha thalassemia hemoglobinopathy, anemia of a chronic disease or a neoplastic disorder, anemia of a hemoglobinopathy, B12 and/or folate deficiency, hematological disease, chronic disease secondary to liver disease with or without alcohol, iron deficiency, acute or chronic phase reaction, dimorphic anemia and gastrointestinal bleeding, the method comprising:

(a-i) obtaining or having obtained a blood sample from an individual having anemia;

(a-ii) testing the blood sample for blood parameters comprising: mean corpuscular hemoglobin concentration (MCHC) level, reticulocyte count, hemoglobin level, mean corpuscular volume (MCV), ferritin level, B12 level, folate level, methylmalonic acid content, one or more markers of liver function, and C-reactive protein (CRP) level;

(a-iii) measuring the blood parameters in the blood sample; and (a-iv) selecting and evaluating the measured blood parameters in each of the following specific combinations to detect a cause of anemia:

(b) if the blood sample MCHC level is elevated compared to a defined standard for MCHC and the blood sample reticulocyte count is normal or elevated compared to a defined standard reticulocyte count, sickle cell anemia or hereditary spherocytosis is detected;

(c) if the blood sample MCHC level is low or normal compared to the defined standard for MCHC or if the blood sample reticulocyte count is low compared to the defined standard reticulocyte count, and the blood sample hemoglobin level is not lower than a defined cutoff for hemoglobin, anemia of a chronic disease or a neoplastic disorder is detected;

(d) if the blood sample MCHC level is low or normal compared to the defined standard for MCHC, the blood sample hemoglobin level is lower than a defined cutoff for hemoglobin, the blood sample MCV is low compared to a standard for MCV, and the blood sample ferritin level is low compared to a defined cutoff for ferritin, iron deficiency or alpha thalassemia hemoglobinopathy is detected;

(e) if the blood sample MCHC level is low or normal compared to the defined standard for MCHC, the blood sample hemoglobin level is lower than a defined cutoff for hemoglobin, the blood sample MCV is low compared to a standard for MCV, and the blood sample ferritin level is normal or high compared to a defined cutoff for ferritin, then performing a hemoglobinopathy evaluation to detect an anemia of a chronic disease, hemolytic anemia, or anemia of a hemoglobinopathy, wherein:

(e-i) if the blood sample reticulocyte count is normal compared to the defined standard reticulocyte count and the hemoglobinopathy evaluation is normal, anemia of a chronic disease is detected;

(e-ii) if the blood sample reticulocyte count is elevated compared to the defined standard reticulocyte count and the hemoglobinopathy evaluation is normal, hemolytic anemia is detected; or (e-iii) if the blood sample reticulocyte count is normal or elevated compared to the defined standard reticulocyte count and the hemoglobinopathy evaluation is abnormal, anemia of a hemoglobinopathy is detected;

(f) if the blood sample MCHC level is low or normal compared to the defined standard for MCHC, the blood sample hemoglobin level is lower than a defined cutoff for hemoglobin, the blood sample MCV is elevated by at least 10% compared to a standard for MCV, and the blood sample ferritin level is normal or high compared to a defined cutoff for ferritin, the blood sample B12 and/or folate levels are lower than defined cutoffs for B12 and/or folate, and the blood sample methylmalonic acid content is elevated, a B12 and/or folate deficiency is detected;

(g) if the blood sample MCHC level is low or normal compared to the defined standard for MCHC, the blood sample hemoglobin level is lower than a defined cutoff for hemoglobin, the blood sample MCV is elevated by at least 10% compared to a standard for MCV, and the blood sample ferritin level is normal or high compared to a defined cutoff for ferritin, the blood sample B12 and/or folate levels are higher than defined cutoffs for B12 and/or folate, and the blood sample reticulocyte count is normal or elevated compared to the defined standard reticulocyte count, sickle cell anemia or hereditary spherocytosis is detected;

(h) if the blood sample MCHC level is low or normal compared to the defined standard for MCHC, the blood sample hemoglobin level is lower than a defined cutoff for hemoglobin, the blood sample MCV is elevated by at least 10% compared to a standard for MCV, and the blood sample ferritin level is normal or high compared to a defined cutoff for ferritin, the blood sample B12 and/or folate levels are higher than defined cutoffs for B12 and/or folate, and the blood sample reticulocyte count is low compared to the defined standard reticulocyte count, then performing a hepatic function panel to detect a hematological disease or chronic disease secondary to liver disease with or without alcohol, wherein:

(h-i) if the blood sample one or more markers of liver function are within the a defined range for the one or more markers of liver function, hematological disease is detected; or (h-ii) if the blood sample one or more markers of liver function are not within the defined range for the one or more markers of liver function, chronic disease secondary to liver disease with or without alcohol is detected;

(i) if the blood sample MCHC level is low or normal compared to the defined standard for MCHC, the blood sample hemoglobin level is lower than a defined cutoff for hemoglobin, the blood sample MCV is normal compared to a standard for MCV, and the blood sample ferritin level is low compared to a defined cutoff for ferritin, iron deficiency is detected;

(j) if the blood sample MCHC level is low or normal compared to the defined standard for MCHC, the blood sample hemoglobin level is lower than a defined cutoff for hemoglobin, the blood sample MCV is normal compared to a standard for MCV, and the blood sample ferritin level is high compared to a defined cutoff for ferritin, acute or chronic phase reaction is detected;

(k) if the blood sample MCHC level is low or normal compared to the defined standard for MCHC, the blood sample hemoglobin level is lower than a defined cutoff for hemoglobin, the blood sample MCV is normal compared to a standard for MCV, the blood sample ferritin level is normal compared to a defined cutoff for ferritin, the blood sample reticulocyte count is normal compared to the defined standard reticulocyte count, and the blood sample C-reactive protein (CRP) level is normal compared to a defined cutoff for CRP level, anemia of a chronic disease or dimorphic anemia is detected;

(l) if the blood sample MCHC level is low or normal compared to the defined standard for MCHC, the blood sample hemoglobin level is lower than a defined cutoff for hemoglobin, the blood sample MCV is normal compared to a standard for MCV, the blood sample ferritin level is normal compared to a defined cutoff for ferritin, the blood sample reticulocyte count is elevated compared to the defined standard reticulocyte count, and the blood sample C-reactive protein (CRP) level is normal compared to a defined cutoff for CRP level, hemolytic anemia or gastrointestinal bleeding is detected; and (m) if the blood sample MCHC level is low or normal compared to the defined standard for MCHC, the blood sample hemoglobin level is lower than a defined cutoff for hemoglobin, the blood sample MCV is normal compared to a standard for MCV, the blood sample ferritin level is normal compared to a defined cutoff for ferritin, the blood sample reticulocyte count is low or normal compared to the defined standard reticulocyte count, and the blood sample C-reactive protein (CRP) level is elevated compared to a defined cutoff for CRP level, then performing a complete metabolic panel (CMP) wherein if the CMP is abnormal, anemia of a chronic disease is detected.

2. The method of claim 1, wherein if sickle cell anemia or hereditary spherocytosis is detected, the method further comprises performing genetic testing for sickle cell anemia or hereditary spherocytosis.

3. The method of claim 1, wherein the defined cutoff for hemoglobin is about 13.2 mg/l for an adult male and about 11.7 mg/l for an adult female.

4. The method of claim 1, wherein the hemoglobinopathy evaluation comprises measuring hemoglobin A, hemoglobin F, total hemoglobin, hemoglobin A2, hemoglobin S, hemoglobin C, hemoglobin E and any hemoglobin variants.

5. The method of claim 4, wherein the hemoglobinopathy evaluation further comprises measuring a red blood cell count, measuring hematocrit, measuring mean corpuscular volume (MCV), measuring mean corpuscular hemoglobin (MCH), and measuring red blood cell distribution width (RDW).

6. The method of claim 1, wherein the hematological disease is myelodysplasia or a hematological malignancy.

7. The method of claim 1, wherein only a single blood sample is obtained from the individual.

8. The method of claim 1, wherein steps (a-i)-(a-ii) are completed in 72 hours or less.

9. The method of claim 1, wherein the hepatic function panel comprises measuring a level of total protein, albumin, bilirubin, alkaline phosphatase (ALP), alanine transaminase (ALT), and aspartate aminotransferase (AST).

10. An automated process for generating an anemia profile of an individual having or suspected of having anemia comprising:

obtaining or having obtained a blood sample from the individual having or suspected of having anemia;

testing the blood sample for blood parameters comprising: a hemoglobin level, mean corpuscular hemoglobin concentration (MCHC), and mean corpuscular volume (MCV);

measuring the blood sample hemoglobin level, blood sample MCHC level, and blood sample MCV value by using one or more processing modules; and generating an anemia profile of the individual having or suspected of having anemia by selecting and evaluating the measured blood sample hemoglobin level, the blood sample MCHC level, and the blood sample MCV value in each of the following specific combinations:

i) if the blood sample MCHC level is elevated compared to a defined standard for MCHC then an MCHC-elevated anemia is detected;

ii) if the blood sample hemoglobin level is lower than a defined standard for hemoglobin level, the blood sample MCV is lower than a defined standard for MCV, and the blood sample MCHC level is normal or lower than the defined standard for MCHC, then a microcytic anemia is detected;

iii) if the blood sample hemoglobin level is lower than the defined standard for hemoglobin level, the blood sample MCV is normal compared to the defined standard for MCV, and the blood sample MCHC level is normal or lower than the defined standard for MCHC, then a normocytic anemia is detected; and iv) if the blood sample hemoglobin level is lower than the defined standard for hemoglobin level, and the MCV is elevated by at least about 10% compared to the defined standard for MCV, then a macrocytic anemia is detected.

11. The automated process of claim 10, further comprising automatically measuring a blood sample reticulocyte count by the same one or more processing modules and/or at least an additional processing module following step i), wherein if the blood sample reticulocyte count is elevated compared to a defined standard for reticulocyte count, then the MCHC-elevated-anemia is caused by a hemolytic anemia or gastrointestinal bleeding.

12. The automated process of claim 11, wherein the hemolytic anemia comprises sickle cell anemia, hereditary spherocytosis, or an acquired hemolytic anemia.

13. The automated process of claim 10, further comprising automatically measuring a blood sample reticulocyte count, measuring a blood sample ferritin level, and performing hemoglobinopathy evaluation by the same one or more processing modules and/or at least an additional processing module following step ii), wherein if the blood sample ferritin level is reduced compared to a defined standard level of ferritin, an iron deficiency is detected.

14. The automated process of claim 10, further comprising automatically measuring a blood sample reticulocyte count, measuring a blood sample ferritin level, and performing a hemoglobinopathy evaluation by the same one or more processing modules and/or at least an additional processing module following step ii), wherein:

a) if the blood sample has a normal or elevated level of ferritin, a normal hemoglobinopathy evaluation and a normal reticulocyte count, an anemia of chronic disease is detected;

b) if the blood sample has a normal or elevated level of ferritin, a normal hemoglobinopathy evaluation, and an elevated reticulocyte count, a hemolytic anemia is detected; or c) if the blood sample has a normal or elevated level of ferritin, an abnormal hemoglobinopathy evaluation, and a normal or elevated reticulocyte count, an anemia of a hemoglobinopathy is detected.

15. The automated process of claim 10, further comprising automatically measuring a blood sample reticulocyte count, measuring a blood sample ferritin level, measuring a blood sample C-reactive protein (CRP), and performing a comprehensive metabolic panel (CMP) following step iii), wherein if the blood sample has a reduced level of ferritin, an iron deficiency or early iron deficiency is detected.

16. The automated process of claim 10, further comprising automatically measuring a blood sample reticulocyte count, measuring a blood sample ferritin level, measuring a blood sample C-reactive protein (CRP), and performing a comprehensive metabolic panel (CMP) following step iii), wherein if the blood sample has an elevated level of ferritin, an acute phase reaction is detected.

17. The automated process of claim 10, further comprising automatically measuring a blood sample reticulocyte count, measuring a blood sample ferritin level, measuring a blood sample C-reactive protein (CRP), and performing a comprehensive metabolic panel (CMP) following step iii), wherein: a) if the blood sample has a normal level of ferritin and an elevated reticulocyte count, hemolytic anemia or gastrointestinal bleeding is detected; b) if the blood sample has a normal level of ferritin, a low or normal reticulocyte count, an elevated level of CRP, and an abnormal or normal CMP, anemia of chronic disease (ACD) is detected; or c) if the blood sample has a normal level of ferritin, a normal reticulocyte count, and a normal level of CRP, anemia of chronic disease or dimorphic anemia is detected.

18. The automated process of claim 10, further comprising automatically measuring reticulocyte count, measuring folate, measuring vitamin B12, and performing a hepatic function panel by the same one or more processing modules and/or at least an additional processing module following step iv), wherein if the blood sample has either a low level of folate or vitamin B12, folate or vitamin B12 deficiency is detected.

19. The automated process of claim 18, further comprising performing a methylmalonic acid test to confirm a vitamin B12 deficiency.

20. The automated process of claim 10, further comprising automatically measuring reticulocyte count, measuring folate, measuring vitamin B12, and performing a hepatic function panel by the same one or more processing modules and/or at least an additional processing module following step iv), wherein if the blood sample has either a low level of folate or vitamin B12 and an elevated reticulocyte count, hemolytic anemia is detected.

21. The automated process of claim 10, further comprising automatically measuring reticulocyte count, measuring folate, measuring vitamin B12, and performing a hepatic function panel by the same one or more processing modules and/or at least an additional processing module following step iv), wherein: a) if the blood sample has either a low level of folate or vitamin B12, an elevated reticulocyte count, and a normal hepatic function, a hematologic disease is detected; or b) if the blood sample has either a low level of folate or vitamin B12, an elevated reticulocyte count, and an abnormal hepatic function, anemia of chronic disease, optionally secondary to a liver disease, further optionally associated with alcohol is detected.

22. The automated process of claim 10, wherein the hepatic function panel comprises measuring a level of total protein, albumin, bilirubin, alkaline phosphatase (ALP), alanine transaminase (ALT), and aspartate aminotransferase (AST).

23. The automated process of claim 10, wherein the individual having or suspected of having anemia is not suspected of having aplastic anemia.

* * * * *